United States Patent
Otake et al.

(10) Patent No.: US 7,691,860 B2
(45) Date of Patent: Apr. 6, 2010

(54) SULFONAMIDE DERIVATIVES

(75) Inventors: Norikazu Otake, Tsukuba (JP); Yoshio Ogino, Tsukuba (JP); Akio Kanatani, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 808 days.

(21) Appl. No.: 10/589,693

(22) PCT Filed: Feb. 15, 2005

(86) PCT No.: PCT/JP2005/002670

§ 371 (c)(1),
(2), (4) Date: Aug. 17, 2006

(87) PCT Pub. No.: WO2005/080348

PCT Pub. Date: Sep. 1, 2005

(65) Prior Publication Data

US 2008/0161326 A1    Jul. 3, 2008

(30) Foreign Application Priority Data

Feb. 19, 2004    (JP)    ................. 2004-043347

(51) Int. Cl.
| | | |
|---|---|---|
| A61K 31/497 | (2006.01) | |
| A61K 31/52 | (2006.01) | |
| A61K 31/437 | (2006.01) | |
| A61K 31/445 | (2006.01) | |
| A61K 31/4184 | (2006.01) | |
| C07D 257/04 | (2006.01) | |
| C07D 235/04 | (2006.01) | |
| C07D 471/04 | (2006.01) | |
| C07D 473/00 | (2006.01) | |
| C07D 401/00 | (2006.01) | |

(52) U.S. Cl. ............. 514/252.16; 514/263.1; 514/303; 514/322; 514/396; 544/264; 544/362; 544/370; 546/118; 548/250; 548/304.4

(58) Field of Classification Search ............ 514/252.16, 514/263.1, 303, 322, 396; 544/264, 362, 544/370; 546/118; 548/250, 304.4
See application file for complete search history.

(56) References Cited

U.S. PATENT DOCUMENTS

| | | | |
|---|---|---|---|
| 5,149,700 | A | 9/1992 | Ellingboe et al. |
| 6,699,891 | B1 | 3/2004 | Kawanishi et al. |
| 2002/0007071 | A1 | 1/2002 | Britton et al. |

FOREIGN PATENT DOCUMENTS

JP    9-169743    6/1997

WO    WO 01/46189    6/2001

OTHER PUBLICATIONS

Moreno et al., E. Journal of Med. Chem., vol. 39 (2004), pp. 49-58, "Synthesis and evaluation of new arylsulfonamidomethylcyclohexyl derivatives as human neuropeptide Y Y5 receptor antagonists . . . ".

Primary Examiner—Kamal A Saeed
Assistant Examiner—Samantha L Shterengarts
(74) Attorney, Agent, or Firm—Baerbel R. Brown; Catherine D. Fitch

(57) ABSTRACT

The present invention relates to compounds of the general formula (I):

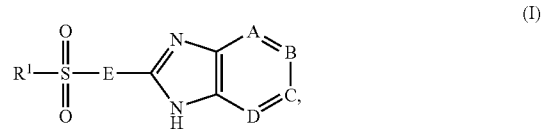

wherein A, B, C and D each independently are a methine group or a nitrogen atom, said methine group optionally having a substituent(s) with at least one of them meaning the methine group; E means a group represented by the following formulae (E1):

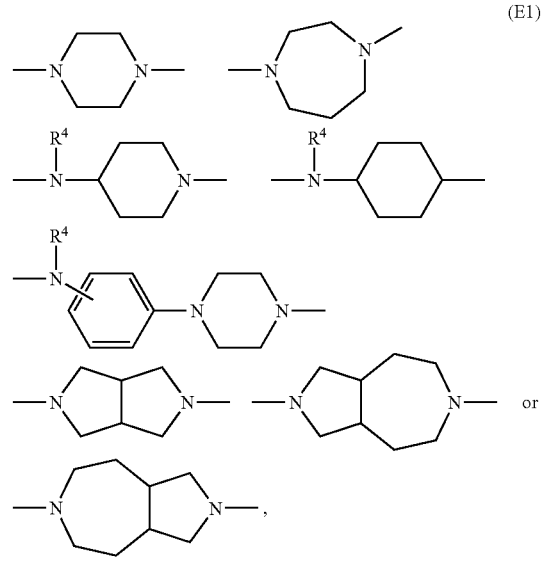

$R^1$ means a lower alkyl group or an aryl group optionally having a substituent(s) or means a lower alkylene group linked to arbitrary, linkable position(s) of E, and others.

The compounds of the present invention are useful as an agent for the treatment of a variety of diseases related to NPY.

10 Claims, No Drawings

SULFONAMIDE DERIVATIVES

TECHNICAL FIELD

The present invention is useful in the medical fields. In more detail, the novel sulfonamide derivatives of the present invention, which act as an antagonist against the neuropeptide Y receptor, are useful as an agent for the treatment of a variety of diseases, inclusive of cardiovascular disorders, neurological diseases, metabolic diseases, reproductive disorders, gastro-intestinal disorders, respiratory disorders, inflammatory diseases or glaucoma, etc.

CROSS-REFERENCE TO RELATED APPLICATIONS

This application is a U.S. national phase application which claims priority under 35 U.S.C. §119 from Japanese Application No. JP2004-043347, filed Feb. 19, 2004.

BACKGROUND OF THE INVENTION

Neuropeptide Y (hereinafter referred to as "NPY"), a peptide consisting of 36 amino acids, was first isolated from the porcine brain by Tatemoto et al in 1982. (Nature, vol. 296, pp. 659 (1982)). NPY is widely distributed in the central and peripheral nervous systems, and performs diverse functions in vivo as one of the most abundant peptides in the nervous system. That is, NPY acts as an orexigenic substance in the central nervous system, and also promotes markedly the fat-accumulation as mediated by the secretion of various hormones and the action of the nervous systems. Continuous intracerebroventricular administration of NPY is known to induce obesity and insulin resistance on the basis of such actions. (International Journal of Obesity, vol. 19, pp. 517 (1995); Endocrinology, vol. 133, pp. 1753 (1993)). It is also known that NPY has central actions, such as depression, anxiety, schizophrenia, pain, dementia and circadian rhythm control, etc (Drugs, vol. 52, pp. 371 (1996); The Journal of Neuroscience, vol. 18, pp. 3014 (1998)). Furthermore, NPY coexists with norepinephrine at the sympathetic nerve terminals in the peripheral nervous system, and is implicated in the tonicity of the sympathetic nerve system. Peripheral administration of NPY is known to cause vasoconstriction and also to reinforce the actions of other vasoconstrictive substances including norepinephrine (British journal of Pharmacology, vol. 95, pp. 419 (1988)). In addition, NPY is also reported to enhance cardiac hypertrophy as a result of the sympathetic stimulation. (Proceedings of the National Academy of Sciences of the United States of America, vol. 97, pp. 1595 (2000)).

Besides, the said peptide is also reported to be involved in the ability to secrete the sex and growth hormones, sexual and reproductive functions, gastro-intestinal motility, bronchoconstriction, inflammation and alcohol preference (Life Sciences, vol. 55, pp. 551 (1994); The Journal of Allergy and Clinical Immunology, vol. 101, pp. S345 (1998); Nature, vol. 396, pp. 366 (1998)).

NPY exhibits diverse pharmacologic activities via the receptors partially shared by its homologues of the peptide YY and pancreatic polypeptide. These pharmacologic activities of NPY are known to be developed by virtue of at least five types of the receptors either solely or through their mutual interactions. (Trends in Neurosciences, vol. 20, pp. 294 (1997)).

It is reported that the central effects mediated by NPY Y1 receptor include remarkable orexigenic effect (Endocrinology, vol. 137, pp. 3177 (1996)); Endocrinology, vol. 141, pp. 1011 (2000));

NPY can develop its functions through binding to the NPY receptors existing in the central nervous system or the peripheral nervous system. Consequently, inhibition of the binding of NPY to the NPY receptor can prevent NPY from developing its actions. In consequence of this, a substance which acts to antagonize the binding of NPY to the NPY receptor can be expected to be useful in the prophylaxis or treatment of various diseases related to NPY, which diseases are exemplified by the cardiovascular disorders, such as angina, acute or congestive heart failure, myocardial infarction, hypertension, nephropathy, electrolyte abnormality and vasospasm, etc.; diseases of the central nervous system, such as bulimia, depression, anxiety, seizure, epilepsy, dementia, pain, alcoholism, drug withdrawal, circadian rhythm disorders, schizophrenia, memory impairment, sleep disorders, and cognitive impairment, etc.; metabolic diseases, such as obesity, diabetes, hormone abnormality, gout, and fatty liver, etc.; genital or reproductive disorders, such as infertility, preterm labor and sexual dysfunction; gastro-intestinal disorders; respiratory disorders; inflammatory diseases; or glaucoma; and the like (Trends in Pharmacological Sciences, vol. 15, pp. 153 (1994); Life Sciences, vol. 55, pp. 551 (1994); Drugs, vol. 52, pp. 371 (1996); The Journal of Allergy and Clinical Immunology, vol. 101, pp. S345 (1998); Nature, vol. 396, pp. 366 (1998); The Journal of Pharmacology and Experimental Therapeutics, vol. 284, pp. 633 (1998); Trends in Pharmacological Sciences, vol. 20, pp. 104 (1999); Proceedings of the National Academy of Sciences of the United States of America, vol. 97, pp. 1595 (2000); The Journal of Neuroscience, vol. 21, pp. 5367 (2001); Pharmacology & Therapeutics, vol. 65, pp. 397 (1995); Endocrinology, vol. 140, pp. 4046 (1999); American Journal of Physiology, vol. 280, pp. R1061 (2001); American Journal of Physiology, vol. 278, pp. R1627 (2000); Current Opinion in Clinical Nutrition and Metabolic Care, vol. 2, pp. 425 (1999); Current Rheumatology Reports, vol. 3, pp. 101 (2001); American Journal of Respiratory and Critical Care Medicine, vol. 165, pp. 1217 (2002)).

In recent years, the present inventors, after their research and investigation, found additionally that certain NPY receptor antagonists are useful in the prophylaxis or treatment of hypercholesteroleamia, hyperlipidemia and arteriosclerosis (refer to the pamphlet of International Patent Application Publication No. 99/27965).

In the pamphlet of International Patent Application Publication No. 01/46189 (Patent Literature No. 1), there are disclosed a variety of benzimidazole derivatives. However, the said literature does neither disclose nor suggest anything about the antagonistic actions against the NPY receptor of the said derivatives and the compounds of the present invention themselves.

Patent Literature No. 1:

The pamphlet of International Patent Application Publication No. WO 01/46189

DETAILED DESCRIPTION OF THE INVENTION

An object of the present invention is to provide a novel medicine having an NPY antagonistic activities.

The present inventors have discovered that a compound of the general formula (I):

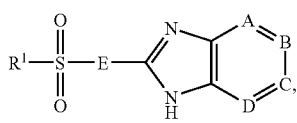

(I)

wherein A, B, C and D each independently mean a methine group or a nitrogen atom, said methine group optionally having a substituent(s) selected from the group consisting of a halogen atom, a cyano group, a lower alkyl group, a $C_3$-$C_9$ cycloalkyl group, a halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N($R^2$)$R^3$, and a group represented by —$Q^1$—$Ar^1$, with at least one of A, B, C and D meaning the methine group;

$Ar^1$ means an aryl group or a heteroaryl group, each of which may optionally have a substituent(s) selected from the group consisting of a halogen atom, a nitro group, a hydroxy group, a lower alkyl group, a halo-lower alkyl group, a hydroxy-lower alkyl group, a $C_3$-$C_6$ cycloalkyl group, a lower alkenyl group, a lower alkoxy group, a halo-lower alkoxy group, a lower alkylthio group, a lower alkylsulfonyl group, a carboxy group, a lower alkanoyl group, a lower alkoxycarbonyl group, a lower alkanoylamino group and a group represented by —$Q^2$—$Ar^2$;

$Ar^2$ means an aryl group or a heteroaryl group, each of which may optionally have a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group;

E means a group represented by the following formulae (E1):

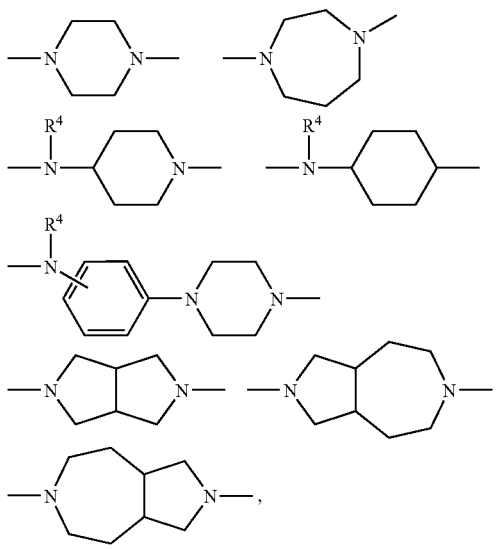

wherein $R^4$ means a hydrogen atom, a lower alkyl group, an aralkyl group or an aryl group; $Q^1$ and $Q^2$ each independently mean a single bond, an oxygen atom, a carbonyl group or a group represented by —N($R^5$)—; $R^1$ means a lower alkyl group or an aryl group, said aryl group optionally having a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group, or means a lower alkylene group linked to arbitrary, linkable position(s) of E; and $R^2$ and $R^3$ each independently mean a hydrogen atom or a lower alkyl group, or are taken together to mean a lower alkylene group which may be intervened by an oxygen atom, a sulfur atom or an imino group; $R^5$ means a hydrogen atom or a lower alkyl group, has NPY antagonistic activities, particularly the antagonistic action at the NPY Y5 receptor, exhibit excellent in vivo pharmacokinetics, for example, in terms of transport or transition into the brain or cerebrospinal fluid, and show an extremely improved degree of safety, thus leading to completion of the present invention.

The compounds (I) of the present invention possess NPY antagonistic activities, particularly the antagonistic actions at the NPY Y5 receptor, exhibit excellent in vivo pharmacokinetics, for example, in terms of transport or transition into the brain or cerebrospinal fluid, and show an enhanced degree of safety. And the compounds are therefore useful as an agent of for the treatment of a variety of diseases related to NPY, which diseases are exemplified by the cardiovascular disorders, such as angina, acute or congestive heart failure, myocardial infarction, hypertension, nephropathy, electrolyte abnormality, vasospasm and artherosclerosis, etc.; central nervous system diseases, such as bulimia, depression, anxiety, seizure, epilepsy, dementia, pain, alcoholism, drug withdrawal, circadian rhythm disorders, schizophrenia, memory impairment, sleep disorders and cognitive impairment, etc.; metabolic diseases, such as obesity, diabetes, hormone abnormality, hypercholesterolemia, hyperlipidemia, gout and fatty liver, etc.; genital or reproductive disorders, such as infertility, preterm labor and sexual dysfunction, etc.; gastro-intestinal disorders; respiratory disorders; inflammatory diseases; or glaucoma; and the like, as well as atherosclerosis; hypogonadism; hyperandrogenism; polycystic ovary syndrome; hirsutism; gastro-intestinal motility disorder; obesity-related gastro-esophageal reflux; obesity-hypoventilation (Pickwickian syndrome); sleep apnea; inflammation; systemic inflammation of the vasculature; osteoarthritis; insulin resistance; brochoconstriction; alcohol preference, metabolic syndrome (syndrome X); Alzheimer's disease; cardiac hypertrophy; left ventricular hypertrophy; hypertriglyceridemia; low HDL cholesterol; cardiovascular disorders, such as coronary heart disease (CHD), cerebrovascular disease, stroke, peripheral vascular diseases and sudden death, etc.; gallbladder diseases; cancers (breast cancer, endometrial cancer, colon cancer); breathlessness; hyperuricemia; impaired fertility; low back pain; increased anesthetic risk; renal system diseases; renal abnormalities, such as dysfunction in body fluid flow, abnormalities of material transportation and renal failure; shock; arrhythmia; symptoms related to surge in sympathomimetic activity during or after operation on coronary artery or gastrointestinal tracts; diseases related to brain or central nervous system, such as cerebral infarction, neurodegeneration or cerebral stroke, cerebrovascular spasm or cerebral hemorrhage; symptoms related to pain or nociception; diseases related to abnormalities in gastrointestinal motility or secretion, such as various ileuses, urinary incontinence and Crohn's disease, etc.; eating disorders, such as anorexia and bulimia, etc.; inflammatory symptoms or diseases; asthma; bronchiole constriction, or diseases related to abnormal secretion of hormones, such as lutenizing hormone, growth hormone, insulin and luteotropic hormone, etc.

Particularly, the compounds (I) of the present invention are useful as an agent of the treatment of, for example, bulimia, obesity, diabetes, and the like.

The present invention relates to the compounds represented by the general formula (I), salts or esters thereof, and production processes and uses thereof.

In the following, the present invention is to be illustrated in more detail, while giving the definitions for the terms as used in the present specification:

The term "halogen atom" refers to fluorine, chlorine, bromine and iodine.

The term "lower alkyl group" refers to straight-chain or branched alkyl groups of 1 to 6 carbon atoms, which are exemplified by methyl, ethyl, propyl, isopropyl, butyl, isobutyl, sec-butyl, tert-butyl, pentyl, isopentyl, hexyl and isohexyl, etc.

The term "halo-lower alkyl group" refers to the above-described lower alkyl groups being substituted at arbitrary, substitutable position(s) with 1 or not less than 2, preferably 1 to 3, of the same or different, above-described halogen atoms, which include, for example, fluoromethyl, difluoromethyl, trifluoromethyl, 2-fluoroethyl, 1,2-difluoroethyl, chloromethyl, 2-chloroethyl, 1,2-dichloroethyl, bromomethyl and iodomethyl, etc.

The term "lower alkoxy group" refers to straight-chain or branched alkoxy groups of 1 to 6 carbon atoms, which are exemplified by methoxy, ethoxy, propoxy, isopropoxy, butoxy, sec-butoxy, isobutoxy, tert-butoxy, pentyloxy, isopentyloxy, hexyloxy and isohexyloxy, etc.

The term "halo-lower alkoxy group" refers to the above-described lower alkoxy groups being substituted at arbitrary, substitutable position(s) with 1 or not less than 2, preferably 1 to 3, of the same or different, above-described halogen atoms, which include, for example, fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy and iodomethoxy, etc.

The term "lower alkoxycarbonyl group" refers to alkoxycarbonyl groups having the above-described lower alkoxy groups, namely alkoxycarbonyl groups of 2 to 7 carbon atoms, which are exemplified by methoxycarbonyl, ethoxycarbonyl, propoxycarbonyl, isopropoxycarbonyl, butoxycarbonyl, isobutoxycarbonyl, tert-butoxycarbonyl and pentyloxycarbonyl, etc.

The term "lower alkylsulfonyl group" refers to straight-chain or branched alkylsulfonyl groups of 1 to 6 carbon atoms, which are exemplified by methylsulfonyl, ethylsulfonyl, propylsulfonyl, isopropylsulfonyl, butylsulfonyl, sec-butylsulfonyl, isobutylsulfonyl, tert-butylsulfonyl, pentylsulfonyl, isopentylsulfonyl, hexylsulfonyl and isohexylsulfonyl, etc.

The term "lower alkylsulfonyloxy group" refers to straight-chain or branched alkylsulfonyloxy groups of 1 to 6 carbon atoms, which are exemplified by methylsulfonyloxy, ethylsulfonyloxy, propylsulfonyloxy, isopropylsulfonyloxy, butylsulfonyloxy, sec-butylsulfonyloxy, isobutylsulfonyloxy, tert-butylsulfonyloxy, pentylsulfonyloxy, isopentylsulfonyloxy, hexylsulfonyloxy and isohexylsulfonyloxy, etc.

The term "hydroxy-lower alkyl group" refers to the above-described lower alkyl groups being substituted with 1 or not less than 2, preferably 1 or 2, of hydroxy groups at arbitrary, substitutable position(s), which are exemplified by hydroxymethyl, 2-hydroxyethyl, 1-hydroxy-1-methylethyl, 1,2-dihydroxyethyl and 3-hydroxypropyl, etc.

The term "$C_3$-$C_6$ cycloalkyl group" refers to cycloalkyl groups of 3 to 6 carbon atoms, which are exemplified by cyclopropyl, cyclobutyl, cyclopentyl and cyclohexyl groups.

The term "$C_3$-$C_9$ cycloalkyl group" refers to cycloalkyl groups of 3 to 9 carbon atoms, which are exemplified by cycloheptyl, cyclooctyl and cyclononyl, etc. in addition to the specific examples given in the above for the $C_3$-$C_6$ cycloalkyl group.

The term "lower alkenyl group" refers to straight-chain or branched alkenyl groups of 2 to 6 carbon atoms, which are exemplified by vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl and 4-pentenyl, etc.

The term "lower alkylthio group" refers to straight-chain or branched alkylthio groups of 1 to 6 carbon atoms, which are exemplified by methylthio, ethylthio, propylthio, isopropylthio, butylthio, sec-butylthio, isobutylthio, tert-butylthio, pentylthio, isopentylthio, hexylthio and isohexylthio, etc.

The term "lower alkanoyl group" refers to alkanoyl groups having the above-described lower alkyl group, namely, alkanoyl groups of 2 to 7 carbon atoms, which include, for example, acetyl, propionyl, butyryl, isobutyryl, valeryl, isovaleryl and pivaloyl, etc.

The term "lower alkanoylamino group" refers to amino groups derived through mono-substitution with the above-described lower alkanoyl groups, which are exemplified by acetylamino, propionylamino, butyrylamino, isobutyrylamino, valerylamino, isovalerylamino and pivaloylamino, etc.

The term "aryl group" includes, for example, phenyl and naphthyl, etc.

The term "heteroaryl" refers to 5- or 6-membered monocyclic heteroaromatic groups containing 1 or not less than 2, preferably 1 to 3, of the same or different heteroatoms selected from the group consisting of oxygen, nitrogen and sulfur; or fused cyclic heteroaromatic groups, said monocyclic heteroaromatic group being fused with the above-mentioned aryl group or fused each other with the same or different said monocyclic heteroaromatic group, which are exemplified by pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyradinyl, pyrimidinyl, pyridazinyl, 1,2,4-triazinyl, 1,3,5-triazinyl, indolyl, benzofuranyl, benzothienyl, benzoimidazolyl, benzoxazolyl, benzoisoxazolyl, benzothiazolyl, benzoisothiazolyl, indazolyl, purinyl, quinolyl, isoquinolyl, phthalazinyl, naphthylidinyl, quinoxalinyl, quinazolinyl, cinnolinyl, pteridinyl and pyrido[3,2-b]pyridyl, etc.

The term "lower alkylamino group" refers to amino groups derived through mono-substitution with the above-described lower alkyl groups, which are exemplified by methylamino, ethylamino, propylamino, isopropylamino, butylamino, sec-butylamino, tert-butylamino, etc.

The term "di-lower alkylamino group" refers to amino groups derived through di-substitution with the same or different, above-described lower alkyl groups, which are exemplified by dimethylamino, diethylamino, ethylmethylamino, dipropylamino, methylpropylamino and diisopropylamino, etc.

The term "lower alkylene group" refers to straight-chain or branched lower alkylene groups of 1 to 6 carbon atoms, which are exemplified by methylene, ethylene, trimethylene, tetramethylene, pentamethylene, hexamethylene, etc.

The term "lower alkylene group which may be intervened by an oxygen atom, a sulfur atom or an imino group" refers to lower alkylene groups of 2 to 5 carbon atoms which are intervened or not intervened by 1 or 2, preferably 1, of an oxygen atom, a sulfur atom or an imino group at any arbitrary, intervenable position(s) of the said alkylene chain, which are exemplified by ethylene, trimethylene, tetramethylene, pentamethylene, 2-oxatetramethylene, 2-oxapentamethylene, 3-oxapentamethylene, 2-thiatetramethylene, 2-thiapentamethylene, 3-thiapentamethylene, 2-azatetramethylene, 2-azapentamethylene and 3-azapentamethylene, etc.

The term "aralkyl" group refers to the above-described lower alkyl groups being substituted with 1 or not less than 2, preferably 1, of the above-described aryl groups at its arbitrary, substitutable position(s), which are exemplified by benzyl, 1-phenylethyl, phenetyl, 1-naphthylmethyl and 2-naphthylmethyl, etc.

The term "salt" of the compound of the general formula (I) refers to any pharmaceutically acceptable, common salts, which are exemplified by base addition salts derived from the compound having a carboxy or hydroxy group(s) by subjecting the carboxy or hydroxy group(s) to a reaction with a base, or acid addition salts derived from the compound having a amino or basic heterocyclic group(s) by subjecting the amino or heterocyclic group(s) to a reaction with an acid.

Said base addition salt includes, for example, alkali metal salts, such as salts with sodium and potassium, etc.; alkaline earth metal salts, such as salts with calcium and magnesium, etc.; ammonium salts; and organic amine salts, such as salts with trimethylamine, triethylamine, dicyclohexylamine, ethanolamine, diethanolamine, triethanolamine, procaine and N,N'-dibenzylethylenediamine, etc.

Said acid addition salt is exemplified by inorganic acid salts, such as salts with hydrochloric acid, sulfuric acid, nitric acid, phosphoric acid and perchloric acid salts, etc.; organic acid salts, such as salts with maleic acid, fumaric acid, tartaric acid, citric acid, ascorbic acid and trifluoroacetic acid, etc.; and sulfonates, such as salts with methanesulfonic acid, isethionic acid, benzensulfonic acid and p-toluenesulfonic acid, etc.

The term "ester" of the compound of the general formula (I) refers to any pharmaceutically acceptable, common esters derived from the carboxy group when the compound has a carboxy group, which are exemplified by esters with lower alkyl groups, such as methyl, ethyl, propyl, isopropyl, butyl, sec-butyl, tert-butyl, pentyl, isopentyl, neopentyl, cyclopropyl, cyclobutyl and cyclopentyl, etc.; esters with aralkyl groups, such as benzyl and phenetyl, etc.; esters with lower alkenyl groups, such as allyl and 2-butenyl groups, etc.; esters with lower-alkoxy lower-alkyl groups, such as methoxymethyl, 2-methoxyethyl and 2-ethoxyethyl, etc.; lower-alkanoyloxy lower-alkyl groups, such as acetoxymethyl, pivaloyloxymethyl, and 1-pivaloyloxyethyl, etc.; esters with lower-alkoxycarbonyl lower-alkyl groups, such as methoxycarbonylmethyl and isopropoxycarbonylmethyl, etc.; carboxy lower-alkyl groups, such as carboxymethyl, etc.; esters with lower-alkoxycarbonyloxy lower-alkyl groups, such as 1-(ethoxycarbonyloxy)ethyl group and 1-(cyclohexyloxycarbonyloxy)ethyl, etc.; esters with carbamoyloxy lower-alkyl groups, such as carbamoyloxymethyl, etc.; ester with phthalidyl group; and esters with (5-substituted-2-oxo-1,3-dioxol-4-yl)methyl groups, such as (5-methyl-2-oxo-1,3-dioxol-4-yl)methyl, etc., and the like.

The term "agent for the treatment" refers to drug or pharmaceutical preparations which are to be applied for the purpose of the therapy and/or prophylaxis of a variety of diseases.

In order to disclose more specifically the compounds of the general formula (I) according to the present invention, the various symbols to be used in the formula (I) are to be explained below in more detail, while making mention of their appropriate, preferable examples:

the symbols A, B, C and D each independently mean a methine group or a nitrogen atom, said methine group optionally having a substituent(s) selected from the group consisting of a halogen atom, a cyano group, a lower alkyl group, a $C_3$-$C_9$ cycloalkyl group, a halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N($R^2$)$R^3$, and a group represented by —$Q^1$—$Ar^1$, with at least one of A, B, C and D meaning the methine group.

The phrase "a methine group optionally having a substituent(s) selected from the group consisting of a halogen atom, a cyano group, a lower alkyl group, a $C_3$-$C_9$ cycloalkyl group, a halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N($R^2$)$R^3$, and a group represented by —$Q^1$—$Ar^1$" refers to an unsubstituted methine group or a methine group which has a substituent(s), and said substituent can be selected from the group consisting of a halogen atom, a cyano group, a lower alkyl group, a $C_3$-$C_9$ cycloalkyl group, a halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N($R^2$)$R^3$ and a group represented by —$Q^1$—$Ar^1$.

The halogen atom as said substituent preferably includes, for example, fluorine and chlorine, etc.

The lower alkyl group as said substituent preferably includes, for example, methyl and ethyl, etc.

The $C_3$-$C_9$ cycloalkyl group as said substituent preferably includes, for example, cyclopentyl, cyclohexyl and cycloheptyl, etc.

The halo-lower alkyl group as said substituent preferably includes, for example, difluoromethyl and trifluoromethyl, etc.

The lower alkoxy group as said substituent preferably includes, for example, methoxy and ethoxy, etc.

The halo-lower alkoxy group as said substituent preferably includes, for example, difluoromethoxy and trifluoromethoxy, etc.

The lower alkoxycarbonyl group as said substituent preferably includes, for example, methoxycarbonyl and ethoxycarbonyl, etc.

The lower alkylsulfonyl group as said substituent preferably includes, for example, methylsulfonyl and ethylsulfonyl, etc.

The lower alkylsulfonyloxy group as said substituent preferably includes, for example, methylsulfonyloxy and ethylsulfonyloxy, etc.

In the group represented by —N($R^2$)$R^3$ as said substituent, $R^2$ and $R^3$ each independently mean a hydrogen atom or a lower alkyl group, or are taken together to mean a lower alkylene group which may be intervened by an oxygen atom, a sulfur atom or an imino group.

The lower alkyl group as $R^2$ and $R^3$ preferably includes, for example, methyl, ethyl and propyl, etc.

"The lower alkylene group which may be intervened by an oxygen atom, a sulfur atom or an imino group" formed by taking $R^2$ and $R^3$ together preferably includes, for example, pentamethylene and 3-oxapentamethylene, etc. which are taken together with the adjacent nitrogen atom to form, for example, piperidino and morpholino, etc.

The preferable embodiments of $R^2$ and $R^3$ include, for example, a case where at least one of $R^2$ and $R^3$ is a lower alkyl, or a case where $R^2$ and $R^3$ are taken together to form a lower alkylene group which may be intervened by an oxygen atom, a sulfur atom or an imino group.

The group represented by —N($R^2$)$R^3$, consequently, preferably includes, for example, amino, methylamino, ethylamino, propylamino, dimethylamino, diethylamino, ethylmethylamino, 1-azetidinyl, 1-pyrrolidinyl, piperidino, morpholino, thiomorpholino and 1-piperazinyl, etc., among which preferable are methylamino, dimethylamino, piperidino and morpholino, etc.

In the group represented by —$Q^1$—$Ar^1$ as said substituent, $Ar^1$ means an aryl group or a heteroaryl group, each of which may optionally have a substituent(s) selected from the group consisting of a halogen atom, a nitro group, a hydroxy group, a lower alkyl group, a halo-lower alkyl group, a hydroxy-lower alkyl group, a $C_3$-$C_6$ cycloalkyl group, a lower alkenyl group, a lower alkoxy group, a halo-lower alkoxy group, a lower alkylthio group, a lower alkylsulfonyl group, a carboxy group, a lower alkanoyl group, a lower alkoxycarbonyl group, a lower alkanoylamino group and a group represented by —$Q^2$—$Ar^2$; $Q^1$ means a single bond, an oxygen atom, a carbonyl group or a group represented by —N($R^5$)—.

The phrase "an aryl group or a heteroaryl group, each of which may optionally have a substituent(s) selected from the group consisting of a halogen atom, a nitro group, a hydroxy group, a lower alkyl group, a halo-lower alkyl group, a hydroxy-lower alkyl group, a $C_3$-$C_6$ cycloalkyl group, a lower alkenyl group, a lower alkoxy group, a halo-lower alkoxy group, a lower alkylthio group, a lower alkylsulfonyl group, a carboxy group, a lower alkanoyl group, a lower alkoxycarbonyl group, a lower alkanoylamino group and a group represented by —$Q^2$—$Ar^2$" refers to an unsubstituted aryl group or an unsubstituted heteroaryl group mentioned above; or an aryl or a heteroaryl group mentioned above, each of which has a substituent(s) at arbitrary, substitutable position(s), wherein as said substituent group(s), 1 or not less than 2, preferably 1 or 2, of the same or different groups can be selected from the group consisting of a halogen atom, a nitro group, a hydroxy group, a lower alkyl group, a halo-lower alkyl group, a hydroxy-lower alkyl group, a $C_3$-$C_6$ cycloalkyl group, a lower alkenyl group, a lower alkoxy group, a halo-lower alkoxy group, a lower alkylthio group, a lower alkylsulfonyl group, a carboxy group, a lower alkanoyl group, a lower alkoxycarbonyl group, a lower alkanoylamino group and a group represented by —$Q^2$—$Ar^2$.

The halogen atom as said substituent preferably includes, for example, fluorine, chlorine and bromine, etc.

The lower alkyl group as said substituent preferably includes, for example, methyl, ethyl, propyl and isopropyl, etc.

The halo-lower alkyl group as said substituent preferably includes, for example, difluoromethyl and trifluoromethyl, etc.

The hydroxy-lower alkyl group as said substituent preferably includes, for example, hydroxymethyl, 2-hydroxyethyl and 1-hydroxy-1-methylethyl, etc.

The $C_3$-$C_6$ cycloalkyl group as said substituent preferably includes, for example, cyclopropyl and cyclobutyl, etc.

The lower alkenyl group as said substituent preferably includes, for example, vinyl, 1-propenyl and 2-methyl-1-propenyl, etc.

The lower alkoxy group as said substituent preferably includes, for example, methoxy and ethoxy, etc.

The halo-lower alkoxy group as said substituent preferably includes, for example, fluoromethoxy, difluoromethoxy and trifluoromethoxy, etc.

The lower alkylthio group as said substituent preferably includes, for example, methylthio and ethylthio, etc.

The lower alkylsulfonyl group as said substituent preferably includes, for example, methylsulfonyl, ethylsulfonyl and propylsulfonyl, etc.

The lower alkanoyl group as said substituent preferably includes, for example, acetyl and propionyl, etc.

The lower alkoxycarbonyl group as said substituent preferably includes, for example, methoxycarbonyl and ethoxycarbonyl, etc.

The lower alkanoylamino group as said substituent preferably includes, for example, acetylamino and propanoylamino, etc.

In the group represented by —$Q^2$—$Ar^2$ as said substituent, $Ar^2$ means an aryl group or a heteroaryl group, each of which may optionally have a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group; $Q^2$ means a single bond, an oxygen atom, a carbonyl group or a group represented by —N($R^5$)—.

The phrase "an aryl group or a heteroaryl group, each of which may optionally have a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group" means an unsubstituted aryl group or an unsubstituted heteroaryl group mentioned above; or an aryl group mentioned above or a hetero-aryl group mentioned above, each of which has a substituent(s) at arbitrary, substitutable position(s), wherein as the said substituent(s), 1 or not less than 2, preferably 1 or 2, of the same or different groups can be selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group.

The halogen atom as said substituent preferably includes, for example, fluorine and chlorine, etc.

The lower alkyl group as said substituent preferably includes, for example, methyl, ethyl, propyl and isopropyl, etc.

The halo-lower alkyl group as said substituent preferably includes, for example, difluoromethyl and trifluoromethyl, etc.

The hydroxy-lower alkyl group as said substituent preferably includes, for example, hydroxymethyl, 2-hydroxyethyl and 1-hydroxy-1-methylethyl, etc.

The lower alkoxy group as said substituent preferably includes, for example, methoxy and ethoxy, etc.

The halo-lower alkoxy group as said substituent preferably includes, for example, fluoromethoxy, difluoromethoxy and trifluoromethoxy, etc.

The lower alkylamino group as said substituent preferably includes, for example, methylamino and ethylamino, etc.

The di-lower alkylamino group as said substituent preferably includes, for example, dimethylamino and diethylamino, etc.

The lower alkanoyl group as said substituent preferably includes, for example, acetyl and propionyl, etc.

The aryl group as said substituent preferably includes, for example, a phenyl, etc.

The substituent of Ar² preferably includes, for example, a halogen atom, a cyano group, a lower alkyl group, a halo-lower alkyl group, a hydroxy-lower alkyl group, a hydroxy group and a halo-lower alkoxy group, etc.

The aryl group as Ar² preferably includes, for example, a phenyl group, etc., while the heteroaryl group as Ar² preferably includes, for example, pyridyl and quinolyl, etc.

In the group represented by —N(R⁵) as Q¹ and Q², R⁵ means a hydrogen atom or a lower alkyl group.

R⁵ preferably includes, for example, a hydrogen atom, a methyl group and an ethyl, etc.

Q² preferably includes, for example, a single bond, etc.

The substituent of Ar¹ preferably includes, for example, a halogen atom, a hydroxy group, a lower alkyl group, a halo-lower alkyl group, a lower alkenyl group, a lower alkoxy group, a lower alkanoyl group, and a group represented by —Q²—Ar², more preferably a halogen atom, a lower alkyl group and a halo-lower alkyl group, etc.

The aryl group as Ar¹ preferably includes, for example, phenyl group, etc., while the heteroaryl group preferably includes, for example, imidazolyl, furyl, thienyl, pyrazolyl, thiazolyl, oxazolyl, isoxazolyl, tetrazolyl, 1,2,4-oxadiazolyl, 1,3,4-oxadiazolyl, pyridyl, pyrazinyl, pyrimidinyl, benzofuranyl and quinolyl, etc., more preferably tetrazolyl, pyridyl and quinolyl, etc., furthermore more preferably tetrazolyl, etc.

The group represented by Ar¹, consequently, preferably includes, for example, phenyl, 2-fluorophenyl, 3-fluorophenyl, 4-fluorophenyl, 2,3-difluorophenyl, 2,4-difluorophenyl, 2,6-difluorophenyl, 3,5-difluorophenyl, 2-chlorophenyl, 3-chlorophenyl, 4-chlorophenyl, 2-bromophenyl, 3-bromophenyl, 4-bromophenyl, 2-chloro-4-fluorophenyl, 2-chloro-5-fluorophenyl, 2-chloro-6-fluorophenyl, 2-bromo-4-fluorophenyl, 2-bromo-5-fluorophenyl, 2-methylphenyl, 3-methylphenyl, 4-methylphenyl, 5-fluoro-2-methylphenyl, 3-fluoromethylphenyl, 2-trifluoromethylphenyl, 3-trifluoromethylphenyl, 4-trifluoromethylphenyl, 2-methoxyphenyl, 3-methoxyphenyl, 4-methoxyphenyl, 5-fluoro-2-methoxyphenyl, 3-fluoromethoxyphenyl, 2-difluoromethoxyphenyl, 3-difluoromethoxyphenyl, 2-hydroxy-4-fluorophenyl, 2-hydroxymethylphenyl, 3-hydroxymethylphenyl, 3-hydroxyphenyl, 4-hydroxyphenyl, 2-imidazolyl, 2-furyl, 2-thienyl, 2-methyl-5-tetrazolyl, 1,2,4-oxadiazol-5-yl, 1,3,4-oxadiazol-2-yl, 1,2,4-thiadiazol-5-yl, 1,3,4-thiadiazol-2-yl, 2-pyridyl, 3-pyridyl, 4-pyridyl, 2-fluoro-5-pyridyl, 3-fluoro-6-pyridyl, 2-pyrimidinyl, 4-benzo[b]furanyl, 5-benzo[b]furanyl, 7-benzo[b]furanyl, 2-quinolyl, 3-quinolyl, 4-quinolyl, 5-quinolyl, 6-quinolyl and 8-quinolyl, etc., among which more preferable are phenyl, 2-fluorophenyl, 4-fluorophenyl, 2,4-difluorophenyl, 2,5-difluorophenyl, 2-chloro-4-fluorophenyl, 2-chloro-5-fluorophenyl, 2-trifluoromethylphenyl, 2-methyl-5-tetrazolyl, 2-pyridyl, 2-fluoro-5-pyridyl, 3-fluoro-6-pyridyl, 7-benzo[b]furanyl, 2-quinolyl and 3-quinolyl, etc., among which furthermore preferable are phenyl, 2-fluorophenyl, 4-fluorophenyl, 2,4-difluorophenyl and 2-methyl-5-tetrazolyl, etc.

Q¹ preferably includes, for example, a single bond, an oxygen atom and a group represented by —N(R⁵)—, etc., more preferably a single bond, etc.

The substituent of the methine group represented by A, B, C or D preferably includes, for example, a halogen atom, a halo-lower alkyl group, a lower alkoxycarbonyl group, a group represented by —N(R²)R³, and a group represented by —Q¹—Ar¹, etc., more preferably a halo-lower alkyl group and a group represented by —Q¹—Ar¹, etc., furthermore preferably a group represented by —Q¹—Ar¹, etc.

The preferred embodiment of A, B, C and D includes, for example, a case where A and D are the same or different and each means an unsubstituted methine or a nitrogen atom, while either one of B and C is a methine group having a halo-lower alkyl group or a group represented by —Q¹—Ar¹, with the other being an unsubstituted methine group or a nitrogen atom, etc. The more preferable embodiments of A, B, C and D include, for example, a case where A, B and D each are an unsubstituted methine group, while C is a methine group having a halo-lower alkyl group or a group represented by —Q¹—Ar¹; and a case where A is an unsubstituted methine group and B and/or D is/are a nitrogen atom(s), while C is a methine group having a halo-lower alkyl group or a group represented by —Q¹—Ar¹, etc.

More particularly, in the general formula (I), examples of the group represented by the formula (a):

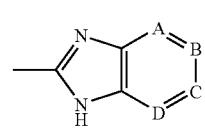

(a)

include, for example, the groups represented by the following formulae (a₁):

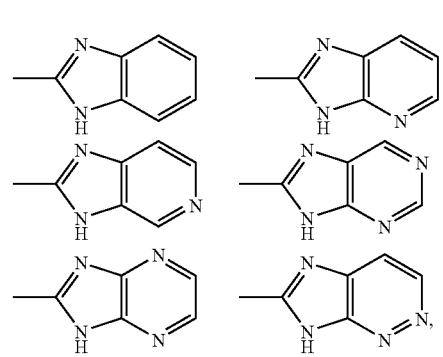

(a₁)

wherein the methine group in such groups may be optionally substituted by a substitutent (s) selected from the group consisting of a halogen atom, a cyano group, a lower alkyl group, a C₃-C₉ cycloalkyl group, halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N(R²)R³ and a group represented by —Q¹—Ar¹, etc.

Among those formulae, preferable examples include the groups represented by the following formulae (a₂):

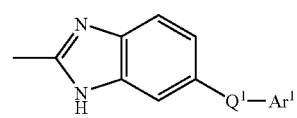

(a₂)

-continued

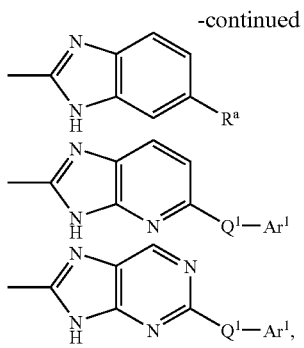

wherein $R^a$ means a halo-lower alkyl group; $Ar^1$ and $Q^1$ are as defined hereinbefore.

E means a group represented by the following formulae (E1):

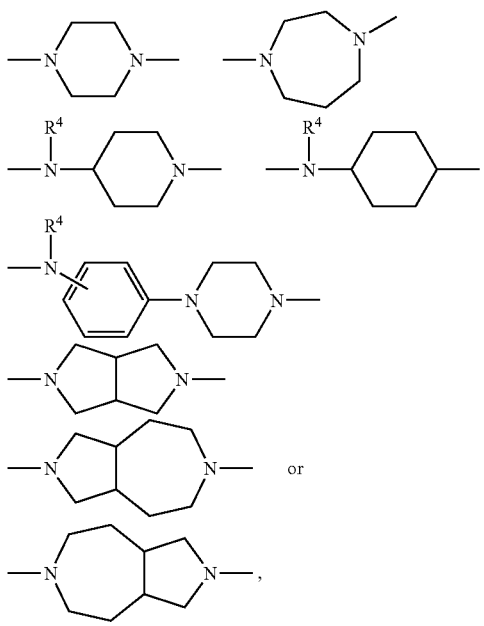

(E1)

etc., wherein $R^4$ means a hydrogen atom, or a lower alkyl group, an aralkyl group or an aryl group.

The lower alkyl group represented by $R^4$ preferably includes, for example, methyl, ethyl and propyl, etc.

The aralkyl group represented by $R^4$ preferably includes, for example, a benzyl.

The aryl group represented by $R^4$ suitably includes, for example, a phenyl, etc.

$R^4$ preferably includes, for example, a hydrogen atom, etc.

E preferably includes, for example, the groups represented by the following formulae (E10):

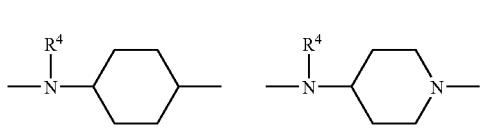

(E10)

-continued

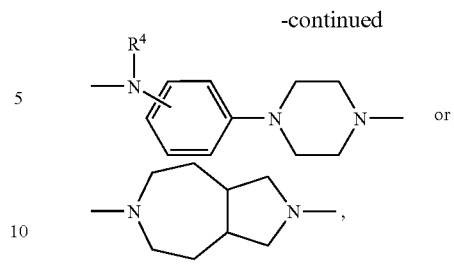

etc., wherein $R^4$ is as defined hereinbefore, among which more preferred examples of E include the groups represented by the following formulae (E11):

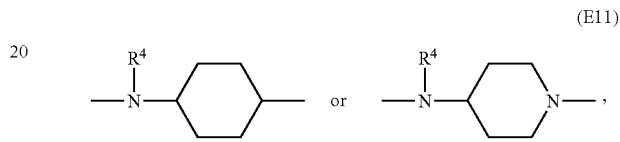

(E11)

etc., wherein $R^4$ is as defined hereinbefore.

$R^1$ means a lower alkyl group or an aryl group, said aryl group optionally having a substitutent (s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group, or means a lower alkylene group which is linked to arbitrary, linkable position(s) of E.

The lower alkyl as $R^1$ preferably includes, for example, methyl, ethyl, isopropyl and tert-butyl, etc., with a tert-butyl being particularly preferable.

The phrase "an aryl group, said aryl group optionally having a substitutent (s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group" refers to an unsubstituted aryl group mentioned above or an aryl group which has a substituent(s) at arbitrary, substitutable position(s) mentioned above, wherein as said substituent(s), 1 or not less than 2, preferably 1 or 2 of the same or different groups can be selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group.

The halogen atom as said substituent preferably includes, for example, fluorine, chlorine and bromine, etc.

The lower alkyl group as said substituent preferably includes, for example, methyl, ethyl, propyl and isopropyl, etc.

The halo-lower alkyl group as said substituent preferably includes, for example, difluoromethyl and trifluoromethyl, etc.

The hydroxy-lower alkyl group as said substituent preferably includes, for example, hydroxymethyl, 2-hydroxyethyl and 1-hydroxy-1-methylethyl, etc.

The lower alkoxy group as said substituent preferably includes, for example, methoxy and ethoxy, etc.

The halo-lower alkoxy group as said substituent preferably includes, for example, fluoromethoxy, difluoromethoxy and trifluoromethoxy, etc.

The lower alkylamino group as said substituent preferably includes, for example, methylamino and ethylamino, etc.

The di-lower alkylamino group as said substituent preferably includes, for example, dimethylamino and diethylamino, etc.

The lower alkanoyl group as said substituent preferably includes, for example, acetyl and propionyl, etc.

The aryl group as said substituent preferably includes, for example, phenyl, etc.

The said substituent preferably includes, for example, lower alkyl, etc.

The aryl group based on the expression "an aryl group, said aryl group optionally having a substituent(s)" as mentioned for $R^1$ preferably includes, for example, phenyl, etc.

The aryl group which may optionally have the said substituent(s) as mentioned for $R^1$, consequently, preferably includes, for example, phenyl, 2-fluorophenyl, 3-fluorophenyl, 4-fluorophenyl, 2,3-difluorophenyl, 2,4-difluorophenyl, 2,6-difluorophenyl, 3,5-difluorophenyl, 2-chlorophenyl, 3-chlorophenyl, 4-chlorophenyl, 2-bromophenyl, 3-bromophenyl, 4-bromophenyl, 2-chloro-4-fluorophenyl, 2-chloro-5-fluorophenyl, 2-chloro-6-fluorophenyl, 2-bromo-4-fluorophenyl, 2-bromo-5-fluorophenyl, 4-cyanophenyl, 2-methylphenyl, 3-methylphenyl, 4-methylphenyl, 5-fluoro-2-methylphenyl, 3-fluoromethylphenyl, 2-trifluoromethylphenyl, 3-trifluoromethylphenyl, 4-trifluoromethylphenyl, 4-hydroxymethylphenyl, 2-methoxyphenyl, 3-methoxyphenyl, 4-methoxyphenyl, 5-fluoro-2-methoxyphenyl, 3-fluoromethoxyphenyl, 2-difluoromethoxyphenyl, 3-difluoromethoxyphenyl, 2-hydroxy-4-fluorophenyl, 2-hydroxymethylphenyl, 3-hydroxymethylphenyl, 3-hydroxyphenyl, 4-hydroxyphenyl, 4-methylaminophenyl, 4-dimethylaminophenyl, 4-acetylphenyl and 4-biphenylyl, etc., among which phenyl and 4-methylphenyl, etc. are more preferable.

The lower alkylene group as $R^1$ preferably includes, for example, methylene, ethylene, trimethylene and tetramethylene, etc., and these are linked to arbitrary, linkable position(s) of E to form a sultam structure.

Therefore, when $R^1$ means "a lower alkylene group which is linked to arbitrary, linkable position(s) of E", the group represented by the following formula (b):

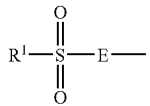
(b)

preferably includes, for example, the groups represented by the following formulae (Ea), and the like:

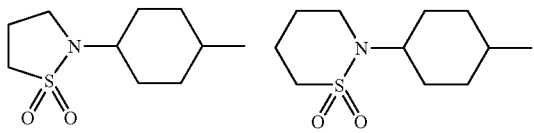
(Ea)

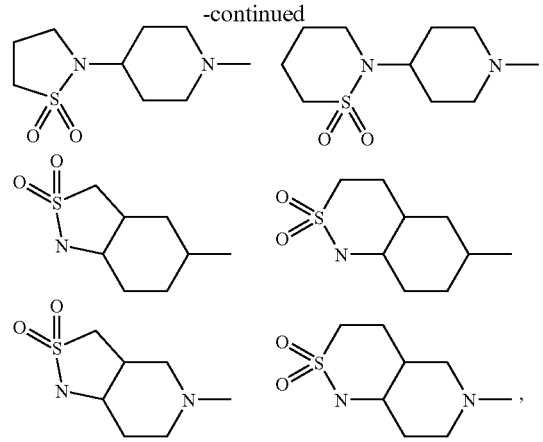
-continued among which more preferable examples include, for example, the group represented by the following formula (Ea1), and the like:

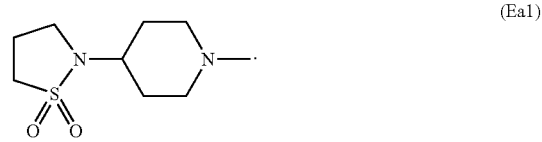
(Ea1)

$R^1$ preferably includes, for example, lower alkyl, etc.

The preferable embodiment of the group represented by the following formula (b):

(b)

includes, for example, a case where $R^1$ is a lower alkyl group, while E is, for example, the group represented by the following formulae (E12):

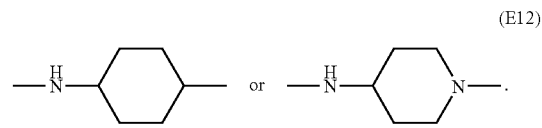
(E12)

The compounds of the present invention, in some cases, exist in the forms of stereo isomers and tautomers, such as optical isomers, diastereo isomers and geometrical isomers, and include all of these stereo isomers, tautomers and their mixtures.

A variety of crystals, hydrates and solvates of the compounds of the present invention are understood to fall into the scope of the present invention.

In addition, the prodrugs of the compounds of the present invention are also understood to fall into the scope of the present invention. Such prodrugs generally constitute any functional derivatives of the compounds of the present invention which are easily convertible in vivo into the required compounds. In the treatment methods of a variety of diseases pertaining to the present invention, therefore, the term "administration" is understood to encompass not only administration of the specifically determined compound, but also administration of any compounds being convertible in vivo into the said specifically determined compound. The conventionally employed means for selection and production of preferable prodrug derivatives is described, for example, in "Design of Prodrugs", ed. H. Bundgaard, Elsevier, 1985, etc., the whole description of which is herein incorporated by reference. The metabolites of these compounds are understood to include any active compounds generated by placing the compound of the present invention in a biological environment, and to fall into the scope of the present invention.

Specific examples of the compounds of the general formula (I) preferably include, for example, 2-(trans-4-tert-butylsulfonylaminocyclohexyl)-5-(trifluoromethyl)benzimidazole,
2-(trans-4-tert-butylsulfonylaminocyclohexyl)-5-(2-methyltetrazol-5-yl)benzimidazole,
2-(trans-4-tert-butylsulfonylaminocyclohexyl)-5-phenylbenzimidazole,
2-(trans-4-tert-butylsulfonylaminocyclohexyl)-5-(2-fluorophenyl)imidazo[4,5-b]pyridine,
8-(trans-4-tert-butylsulfonylaminocyclohexyl)-2-(2-fluorophenyl)purine,
8-(cis-4-tert-butylsulfonylaminocyclohexyl)-2-(2-fluorophenyl)purine,
8-(trans-4-tert-butylsulfonylaminocyclohexyl)-2-(4-fluorophenyl)purine,
8-(cis-4-tert-butylsulfonylaminocyclohexyl)-2-(4-fluorophenyl)purine,
8-(trans-4-tert-butylsulfonylaminocyclohexyl)-2-phenylpurine,
8-(cis-4-tert-butylsulfonylaminocyclohexyl)-2-phenylpurine,
5-(2,4-difluorophenyl)-2-(trans-4-isopropylsulfonylaminocyclohexyl)imidazo[4,5-b]pyridine,
5-(2,4-difluorophenyl)-2-(cis-4-isopropylsulfonylaminocyclohexyl)imidazo[4,5-b]pyridine,
2-(trans-4-methylsulfonylaminocyclohexyl)-5-phenylbenzimidazole,
5-phenyl-2-(trans-4-p-tolylsulfonylaminocyclohexyl)benzimidazole,
2-(cis-4-methylsulfonylaminocyclohexyl)-5-phenylbenzimidazole,
5-phenyl-2-(cis-4-p-tolylsulfonylaminocyclohexyl)benzimidazole,
2-{trans-4-(N-methyl-tert-butylsulfonylamino)cyclohexyl}-5-phenylbenzimidazole,
2-(4-tert-butylsulfonylaminopiperidin-1-yl)-5-phenylbenzimidazole,
2-(4-tert-butylsulfonylaminopiperidin-1-yl)-5-(2-methyltetrazol-5-yl)benzimidazole,
2-(3-isopropylsulfonyl-cis-3,7-diazabicyclo[3.3.0]oct-7-yl)-5-phenylbenzimidazole,
2-(4-isopropylsulfonyl-cis-4,9-diazabicyclo[5.3.0]dec-9-yl)-5-phenylbenzimidazole,
2-(1-isopropylsulfonylpiperazin-4-yl)-5-phenylbenzimidazole,
8-{1-(2-methylsulfonylaminophenyl)piperazin-4-yl}-2-phenylpurine,
5-phenyl-2-{4-(N-phenylmethylsulfonylamino)piperidin-1-yl}-benzimidazole, and
2-{4-(1,1-dioxo-1λ⁶-isothiazolidin-2-yl)piperidin-1-yl}-5-phenylbenzimidazole.

The process for producing the compounds of the present invention is then to be described.

The compounds (I) of the present invention can be produced, for example, by the below-described production processes or the processes to be mentioned in Examples, but the processes for producing the compounds (I) of the present invention are not to be limited thereto.

Production Process I

A compound represented by the general formula (II):

(II)

(wherein $R^{10p}$ is a compound represented by the following formulae (ba1) or (ba2):

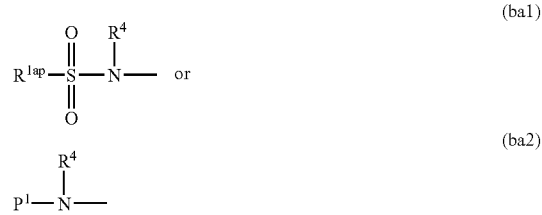

(ba1)

(ba2)

(wherein $R^{1ap}$ means a lower alkyl group or an aryl group, said aryl group optionally having a substituent(s) selected from the group consisting of a halogen atom, a cyano group, a lower alkyl group, a halo-lower alkyl group, a lower alkoxy group, a halo-lower alkoxy group, a lower alkylamino group, a di-lower alkylamino group, a lower alkanoyl group, an aryl group, and an optionally protected hydroxy-lower alkyl group and an optionally protected hydroxyl group, or means a lower alkylene group which is linked to arbitrary, linkable position(s) of a group as represented by the following formula (E1a):

(E1a)

which is formed by being taken together with the cyclohexyl group linked by $R^{10p}$; $P^1$ is an amino- or an imino-protecting group; $R^4$ is as defined herein before), or an azide group) is reacted with a compound represented by the general formula (III):

(III)

(wherein a, b, c and d each independently are a methine group or a nitrogen atom, said methine group optionally having a substituent(s) selected from the group consisting of a halogen atom, a cyano group, a lower alkyl group, a $C_3$-$C_9$ cycloalkyl group, a halo-lower alkyl group, a lower alkoxy group, a halo-lower alkoxy group, a lower alkoxycarbonyl group, a lower alkylsulfonyl group, a lower alkylsulfonyloxy group, a group represented by —N(R$^{2p}$)R$^{3p}$, a group represented by —Q$^{1p}$—Ar$^{1p}$, and an optionally protected hydroxy group, and at least one of a, b, c and d means said methine group; Ar$^{1p}$ means an aryl group or a heteroaryl group which may optionally have a substituent(s) selected from the group consisting of a halogen atom, a nitro group, a lower alkyl group, a halo-lower alkyl group, a $C_3$-$C_6$ cycloalkyl group, a lower alkenyl group, a lower alkoxy group, a halo-lower alkoxy group, a lower alkylthio group, a lower alkylsulfonyl group, a lower alkanoyl group, a lower alkoxycarbonyl group, a lower alkanoylamino group, a group represented by —Q$^2$—Ar$^2$, and an optionally protected hydroxy group, an optionally protected hydroxy-lower alkyl and an optionally protected carboxyl group; Ar$^{2p}$ means an aryl group or a heteroaryl group, each of which may optionally have a substituent(s) selected from the group consisting of a halogen atom, a cyano group, a lower alkyl group, a halo-lower alkyl group, a lower alkoxy group, a halo-lower alkoxy group, a lower alkylamino group, a di-lower alkylamino group, a lower alkanoyl group and an aryl group, an optionally protected hydroxy group and an optionally protected hydroxy-lower alkyl group; Q$^{1p}$ and Q$^{2p}$ each independently mean a single bond, an oxygen atom, an optionally protected carbonyl group or a group represented by —N(R$^5$)—; R$^{2p}$ and R$^{3p}$ each independently mean an amino-protecting group, an imino-protecting group, a hydrogen atom or a lower alkyl group, or are taken together to form a lower alkylene group which may be intervened by an oxygen atom, sulfur atom or an optionally protected imino group; R$^5$ is as defined hereinbefore) or its salt, to give a compound represented by the general formula (IV):

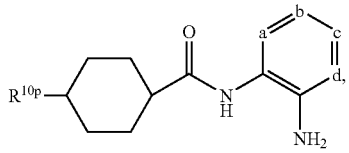

(IV)

wherein a, b, c, d and R$^{10p}$ are as defined hereinbefore, followed by an intramolecular ring closure condensation to form a compound represented by the general formula (V-a):

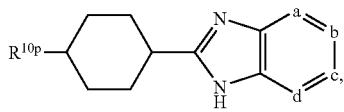

(V-a)

wherein a, b, c, d and R$^{10p}$ are as defined hereinbefore.

i) When R$^{10p}$ is a group represented by the formula (ba1), a protecting group in said compound (V-a) can be optionally removed to prepare a compound represented by the general formula (I-a):

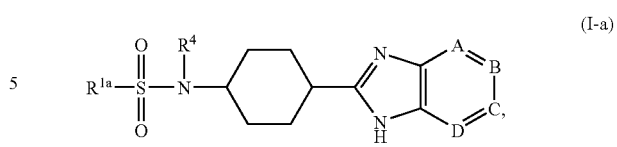

(I-a)

wherein R$^{1a}$ means a lower alkyl group or an aryl group, said aryl group optionally having a substituent(s) selected from the group consisting of a halogen atom, a cyano group, a lower alkyl group, a halo-lower alkyl group, a hydroxy-lower alkyl group, a hydroxy group, a lower alkoxy, a halo-lower alkoxy, a lower alkylamino group, a di-lower alkylamino group, a lower alkanoyl group and an aryl group, or means a lower alkylene group which is linked to arbitrary, linkable position(s) of a group represented by the formula (E1a); A, B, C, D and R$^4$ are as defined hereinbefore;

ii) when R$^{10p}$ is a group represented by the formula (ba2), there is removed the amino-group or imino-protecting group P$^1$; or iii) when R$^{10p}$ is an azide group, the azide group is reduced, followed by a reaction with a compound represented by the general formula (VI):

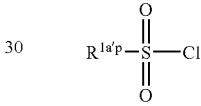

(VI)

(wherein R$^{1a'p}$ means a lower alkyl group or an aryl group, said aryl group optionally having a substituent(s) selected from the group consisting of a halogen atom, a cyano group, a lower alkyl group, a halo-loweralkyl group, a lower alkoxy group, a halo-lower alkoxy group, a lower alkylamino group, a di-lower alkylamino group, a lower alkanoyl group and an aryl group, and optionally protected hydroxy-lower alkyl and optionally protected hydroxy groups) to give a compound represented by the general formula (V-a'):

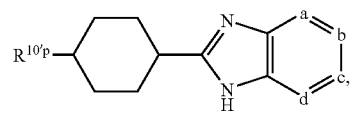

(V-a')

wherein R$^{10p}$ means a group represented by the following formula (ba1):

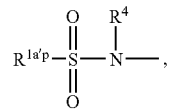

(ba1')

wherein R$^{1a'p}$ and R$^4$ are as defined hereinbefore; and a, b, c and d are as defined hereinbefore), followed by optional removal of the protective group from the said compound (V-a') to prepare a compound represented by the general formula (I-a'):

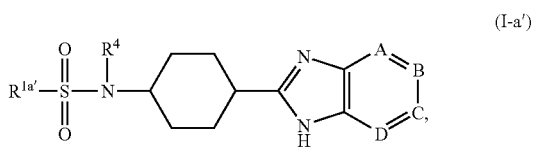

(I-a')

wherein $R^{1a'}$ is a lower alkyl group or an aryl group, said aryl group optionally having a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group; A, B, C, D and $R^4$ are as defined hereinbefore.

The present production process constitutes the production process for a compound of the general formula (I) wherein E is a group represented by the following formula (E1a):

(E1a)

wherein $R^4$ is as defined hereinbefore, namely a compound represented by the general formula (I-a) or (I-a').

In the above-described reactions, when a reactant contains an amino group, an imino group, a hydroxy group, a carboxy group and a carbonyl group, which is not involved in the reactions, the reactions may be carried out after protecting the amino group, the imino group, the hydroxy group, the carboxy group and the carbonyl group with an amino- or an imino-protecting group, an hydroxy-protecting group, a carboxy-protecting group and a carbonyl-protecting group respectively. After the completion of the reactions, such protecting group may be removed.

The "an amino- or imino-protecting group" is not particularly limited, so long as it possesses such protective function, and is exemplified by an aralkyl group, such as benzyl, p-methoxybenzyl, 3,4-dimethoxybenzyl, o-nitrobenzyl, p-nitrobenzyl, benzhydryl and trityl; a lower alkanoyl group, such as formyl, acetyl, propionyl, butyryl and pivaloyl; a benzoyl group; an arylalkanoyl group, such as phenylacetyl and phenoxyacetyl; a lower alkoxycarbonyl group, such as methoxycarbonyl, ethoxycarbonyl, propyloxycarbonyl and tert-butoxycarbonyl groups; an aralkyloxycarbonyl group, such as benzyloxycarbonyl, p-nitrobenzyloxycarbonyl and phenetyloxycarbonyl; a lower alkylsilyl group, such as trimethylsilyl and tert-butyldimethylsilyl; a tetrahydropyranyl group; and a trimethylsilylethoxymethyl group; etc., with acetyl, benzoyl, tert-butoxycarbonyl and trimethylsilylethoxymethyl, etc. being particularly preferable.

The "hydroxy-protecting group" is not particularly limited, so long as it possesses such protective function, and includes, for example, a lower alkyl group, such as methyl, ethyl, propyl, isopropyl and tert-butyl; a lower alkylsilyl group, such as trimethylsilyl and tert-butyldimethylsilyl; a lower alkoxymethyl group, such as methoxymethyl and 2-methoxyethoxymethyl; a tetrahydropyranyl group; a trimethylsilylethoxymethyl group; an aralkyl group, such as benzyl, p-methoxybenzyl, 2,3-dimethoxybenzyl, o-nitrobenzyl, p-nitrobenzyl and trityl; and an acyl group, such as formyl and acetyl; etc., with methyl, methoxymethyl, tetrahydropyranyl, trityl, trimethylsilylethoxymethyl, tert-butyldimethylsilyl and acetyl, etc. being particularly preferred.

The "carboxy-protecting group" is not particularly limited, so long as it possesses such protective function, and includes, for example, a lower alkyl group, such as methyl, ethyl, propyl, isopropyl and tert-butyl; a halo-lower alkyl group, such as 2,2,2-trichloroethyl; a lower alkenyl group, such as 2-propenyl; an aralkyl group, such as benzyl, p-methoxybenzyl, p-nitrobenzyl, benzhydryl and trityl; etc., with methyl, ethyl, tert-butyl, 2-propenyl, benzyl, p-methoxybenzyl and benzhydryl groups, etc. being particularly preferable.

The "carbonyl-protecting group" is not particularly limited, so long as it possesses such protective function, and is exemplified by acetals, ketals and the like, such as ethylene ketal, trimethylene ketal and dimethyl ketal, etc.

The reaction of the carboxylic acid represented by the general formula (II) with the compound represented by the general formula (III) is ordinarily carried out in ratios of 0.5 mole to excessive moles, preferably 1 mole to 1.5 moles, of the carboxylic acid of the general formula (II) against 1 mole of the compound of the general formula (III).

The reaction is generally carried out in an inert solvent, and the said inert solvent preferably includes, for example, methylene chloride, chloroform, tetrahydrofuran, dimethylformamide and pyridine, or mixtures thereof, etc.

The above-mentioned reaction is preferably carried out in the presence of a condensing agent, and as the said condensing agent, use can be made, for example, of N,N'-dicyclohexylcarbodiimide, N,N'-diisopropylcarbodiimide, 1-(3-dimethylaminopropyl)-3-ethyl-carbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidino-phosphonium hexafluorophosphate, bromotris-(dimethylamino)-phosphonium hexafluorophosphate, diphenylphosphoric azide and 1,1-carbonyldiimidazole, etc.

The said condensing agent can ordinarily be used in ratios of 1 mole to excessive mole, preferably from 1 mole to 1.5 moles, against 1 mole of the compound of the general formula (II).

The reaction temperature generally ranges from −50° C. to 100° C., preferably from −20° C. to 50° C.

The reaction time ordinarily ranges from 30 min. to 7 days, preferably from 1 hr. to 24 hrs.

In place of the carboxylic acid represented by the general formula (II), a reactive derivative of the said carboxylic acid can be reacted with the compound represented by the general formula (III) to thereby prepare the compound represented by the general formula (IV).

As the reactive derivative of the carboxylic acid represented by the general formula (II), there can be used, for example, an acid halide, a mixed acid anhydride, an active ester and an active amide, etc.

The acid halide of the carboxylic acid of the general formula (II) can be produced by reacting the carboxylic acid of the general formula (II) with a halogenating agent in accordance with a conventional method. As the halogenating agent, there can be used, for example, thionyl chloride, phosphorus trichloride, phosphorus pentachloride, phosphorus oxychloride, phosphorus tribromide, oxalyl chloride and phosgene, etc.

The mixed acid anhydride of the carboxylic acid of the general formula (II) can be obtained by reacting the carboxylic acid of the general formula (II) with an alkyl chlorocarbonate, such as ethyl chlorocarbonate; and an aliphatic carboxylic acid chloride, such as pivaloyl chloride; etc. in accordance with a conventional method.

The active esters of the carboxylic acid of the general formula (II) can be obtained by reacting the carboxylic acid of the general formula (II) with an N-hydroxy compound, such as N-hydroxysuccinimide, N-hydroxyphthalimide and 1-hydroxybenzotriazole; a phenol compound, such as 4-nitrophenol, 2,4-dinitrophenol, 2,4,5-trichlorophenol and pentachlorophenol; etc. in the presence of a condensing agent including, for example, N,N'-dicyclohexylcarbodiimide and 1-(3-dimethylaminopropyl)-3-ethylcarbodiimide, etc. in accordance with a conventional method.

The active amides of the carboxylic acid of the general formula (II) can be produced, for example, by reacting the carboxylic acid of the general formula (II) with 1,1-carbonyldiimidazole, 1,1-carbonylbis(2-methylimidazole), etc. in accordance with a conventional method.

The reaction of the compound represented by the general formula (III) with a reactive derivative of the carboxylic acid represented by the general formula (II) is generally carried out by using 0.5 mole to excessive moles, preferably 1 mole to 1.5 moles, of the reactive derivative of the carboxylic acid represented by the general formula (II) against 1 mole of the compound represented by the general formula (III).

The reaction is ordinarily carried out in an inert solvent, and the said inert solvent is preferably exemplified by methylene chloride, chloroform, tetrahydrofuran, dimethylformamide and pyridine, and solvent mixtures thereof, etc.

The above-mentioned reaction, though it is allowed to proceed in the absence of a base, is preferably carried out in the presence of a base in order to allow the reaction to proceed smoothly.

As the said base, use can be made, for example, of an organic base, such as triethylamine, diisopropylethylamine, pyridine and 4-dimethylaminopyridine, etc. or an inorganic base, such as sodium hydroxide, potassium hydroxide, sodium carbonate, potassium carbonate and sodium hydrogencarbonate, etc.

The said base can be preferably used in ratios of 1 mole to excessive moles against 1 mole of the compound represented by the general formula (III). When the said base is in the form of liquid, additionally, the said base can also be used as a solvent.

The reaction temperature generally ranges from −50° C. to 100° C., preferably from −20° C. to 50° C.

The reaction time ordinarily ranges from 5 min. to 7 days, preferably from 30 min. to 24 hrs.

After completion of the reaction, the conventional treatment can be conducted to give the compound represented by the general formula (IV) in the form of a crude product. The thus-obtained compound represented by the general formula (IV), after being purified in accordance with a conventional method or directly without being purified, can be subjected to the subsequent intramolecular ring closure condensation.

The intramolecular ring closure condensation for the production of the compound (V-a) from the compound (IV) is ordinarily carried out in an inert solvent or without a solvent.

The said inert solvent is preferably exemplified by ethanol, propanol, butanol, pentanol, 1,4-dioxane, dimethoxyethane, dimethylformadide, dimethylsulfoxide, benzene, toluene, xylene, etc., or solvent mixtures thereof, etc.

The reaction temperature generally ranges from room temperature to the boiling point of the solvent used, preferably from 80° C. to 190° C.

The reaction time ordinarily ranges from 5 hrs. to 7 days, preferably from 12 hrs. to 3 days.

Furthermore, the above ring closure condensation can be conducted in the presence of a dehydrating agent or a catalytic amount of a Lewis acid. The said dehydrating agent is exemplified by cesium fluoride, phosphorus oxychloride, phosphorus pentachloride, polyphosphoric acid and thionyl chloride, etc., and the Lewis acid includes, for example, scandium trifluoromethanesulfonate, yttrium trifluoromethanesulfonate, lanthanum trifluoromethanesulfonate and lanthanide trifluoromethanesulfonate, etc. In such a case, it is preferable to carry out the reaction without a solvent or, for example, in methylene chloride, chloroform, benzene, toluene and xylene, etc. or solvent mixtures thereof, etc.

The amount of the said dehydrating agent used ordinarily ranges from 1 mole to excessive moles, preferably from 2 to 10 moles, against 1 mole of the compound represented by the general formula (IV), while the amount of the said Lewis acid ranges from 10 mole % to 50 mole %, preferably from 10 mole % to 30 mole %.

The preferable reaction temperature generally ranges from room temperature to the boiling point of the solvent used.

The reaction time ordinarily ranges from 1 hr. to 7 days, preferably from 5 hrs. to 3 days.

After completion of the reaction, a conventional treatment can be effected to give the compound represented by the general formula (V-a) in the form of a crude product.

i) The compound represented by the general formula (V-a) wherein $R^{10p}$ is a group represented by the formula (ba1), after being purified in accordance with a conventional method or directly without being purified, can be optionally subjected to a suitable combination of the deprotection reactions for the amino- or imino-protecting group, hydroxy-protecting group, carboxy-protecting group and carbonyl-protecting group to yield the compound of the general formula (I-a).

The deprotection procedure for the protective groups varies depending upon the type of the said protective groups and the stability of the objective compound (I-a), etc., and the deprotection reaction is carried out, for example, in accordance with the procedures as described in literature (refer to "Protective Groups in Organic Synthesis", by T. W. Green, Published by John Wiley & Sons Co. (1981)) or the ones similar thereto, or by a solvolysis with use of an acid or base, namely the procedure which involves, for example, allowing 0.01 mole to a large excess of an acid, preferably trifluoroacetic acid, formic acid and hydrochloric acid, etc., or an equimolar to excessive amounts of a base, preferably potassium hydroxide and calcium hydroxide, etc. to act on the compound; and a chemical reduction with use of a metal hydride complex or a catalytic reduction utilizing a palladium-nickel catalyst and Raney nickel catalyst, etc.

ii) The compound represented by the general formula (V-a) wherein $R^{10p}$ is a group represented by the formula (ba2), after removal of the amino- or imino-protecting group $P^1$, can be reacted with the compound represented by the general formula (VI) in the presence of a base, followed by a conventional treatment to give the compound represented by the general formula (V-a') in the form of a crude product. The thus-obtained compound represented by the general formula (V-a'), after being purified in accordance with a conventional method or directly without being purified, can be optionally subjected to a suitable combination of the deprotection reactions for amino group or imino group, hydroxy group, carboxy group and carbonyl group to produce the compound represented by the general formula (I-a').

The compound of the general formula (V-a) ii) wherein $R^{10p}$ is a group represented by the formula (ba2), is subjected to removal of the protecting group $P^1$ for the amino group or the imino group, or iii) wherein $R^{10p}$ is an azide group, is subjected to reduction of the azide group. The resultant amino compound is reacted with the compound of the general formula (VI), while utilizing the ratios of 1 mole to excessive moles, preferably 1 mole to 1.5 moles, of the compound of the general formula (VI) against 1 mole of the said amine compound.

The reaction is ordinarily carried out in an inert solvent, and the said inert solvent is preferably exemplified by methylene chloride, chloroform, tetrahydrofuran, dimethylformamide and pyridine, etc., or solvent mixtures thereof, etc.

Furthermore, the above-described reaction proceeds even in the absence of a base, but is preferably carried out in the presence of a base in order to allow the reaction to proceed more smoothly.

As the said base, use can be made, for example, of organic bases, such as triethylamine, diisopropylethylamine, pyridine and 4-dimethylaminopyridine, etc., and inorganic bases, such as sodium hydroxide, potassium hydroxide, sodium carbonate, potassium carbonate and sodium hydrogencarbonate, etc.

It is generally suitable to use 1 mole to excessive moles of the said base against 1 mole of the said amine compound. When the said base is in the form of liquid, additionally, it can be used as a solvent.

The reaction temperature generally ranges from −50° C. to 100° C., preferably from −20° C. to 50° C.

The reaction time ordinarily ranges from 5 min. to 2 days, preferably from 30 min. to 24 hrs.

After completion of the reaction, a conventional treatment can be conducted to give the compound represented by the general formula (V-a') in the form of a crude product. The thus-obtained compound represented by the general formula (V-a') can be purified in accordance with a conventional method or deprotected, if necessary, followed by purification or crystallization in accordance with a conventional method to give the objective compound (I-a').

The removal procedure for the protecting groups varies depending upon the type of the protecting groups and the stability of the objective compound (I-a'), etc. and can suitably be conducted, for example, in accordance with the methods as described in the above-described literature or those similar thereto.

The reduction step for the azide group in the compound of the general formula (V-a) wherein $R^{10p}$ is an azide group can be conducted into practice in accordance with a conventional method by effecting catalytic reduction in the presence of a catalyst under the atmosphere of hydrogen or under conditions of triphenylphosphine-water to thereby convert the azide group to an amino group.

Production Process 2

A compound represented by the general formula (VII):

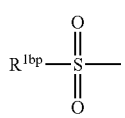

(VII)

(wherein $L^1$ means a leaving group; $P^2$ is an imino-protecting group; a, b, c and d are as defined hereinbefore) is reacted with a compound represented by the general formula (VIII):

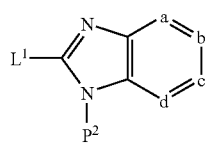

(VIII)

(wherein $R^{1bp}$ means a group represented by the following formula (bb1):

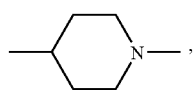

(bb1)

(wherein $R^{1bp}$ means a lower alkyl group or an aryl group, said aryl group optionally having a substituent(s) selected from the group consisting of a halogen atom, a cyano group, a lower alkyl group, a halo-lower alkyl group, a lower alkoxy group, a halo-lower alkoxy group, a lower alkylamino group, a di-lower alkylamino group, a lower alkanoyl group and an aryl group, an optionally protected hydroxy-lower alkyl group and an optionally protected hydroxy group, or means a lower alkylene group which is linked to arbitrary, linkable position(s) of Eb), means an amino- or imino-protecting group, or means an azide group when Eb is a group represented by the following formula (E1b-1):

(E1b-1)

$E^b$ is a group represented by the following formulae (E1b):

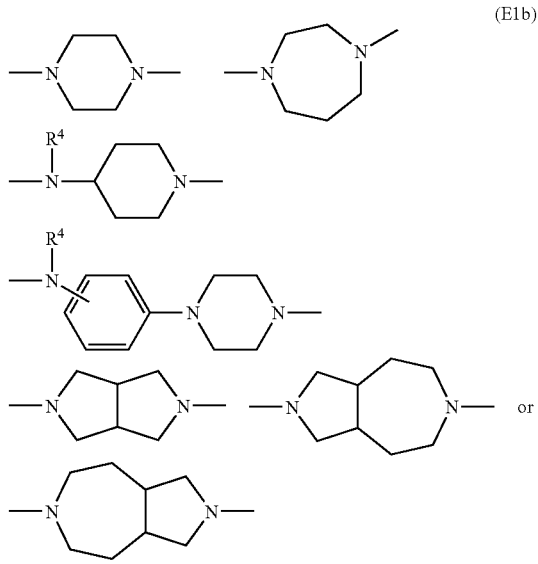

(E1b)

wherein $R^4$ is as defined hereinbefore), or a salt thereof, to give a compound represented by the general formula (V-b):

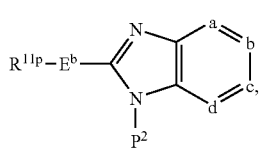

(V-b)

wherein a, b, c, d, $E^b$, $P^2$ and $R^{11p}$ are as defined hereinbefore. i) When $R^{11p}$ is the group represented by the formula (bb1), the protecting group in the said compound (V-b) is optionally removed, to produce a compound represented by the general formula (I-b):

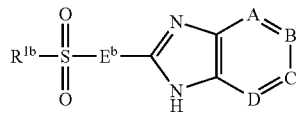

(I-b)

(wherein $R^{1b}$ means a lower alkyl group or an aryl group, said aryl group optionally having a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group, or means a lower alkylene group which is linked to arbitrary, linkable position(s) of $E^b$; A, B, C, D and $E^b$ are as defined hereinbefore]; or ii) when $R^{11p}$ is a protective group for an amino- or imino-group in the compound of the general formula (V-b), an amino- or imino-protecting group is removed and then the said compound is reacted with a compound represented by the general formula (VI):

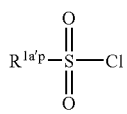

(VI)

(wherein $R^{1a'p}$ is as defined hereinbefore) to give a compound represented by the general formula (V-b'):

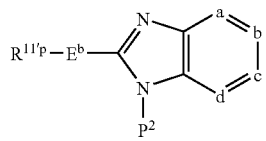

(V-b')

(wherein $R^{11p}$ means a group represented by the following formula (bb1):

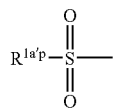

(bb1')

(wherein $R^{1a'p}$ is as defined hereinbefore); a, b, c, d, $E^b$ and $P^2$ are as defined hereinbefore), the protecting group in the said compound (V-b') is optionally removed to thereby produce a compound represented by the general formula (I-b'):

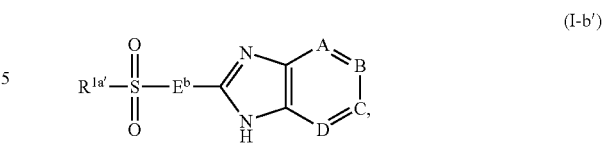

(I-b')

wherein A, B, C, D, E and $R^{1a'}$ are as defined hereinbefore; or iii) when $R^{11p}$ is an azide group in the compound of the general formula (V-b), the azide group is reduced and then the said compound is reacted with a compound represented by the general formula (VI):

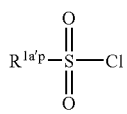

(VI)

(wherein $R^{1a'p}$ is as defined hereinbefore) to give a compound represented by the general formula (V-b"):

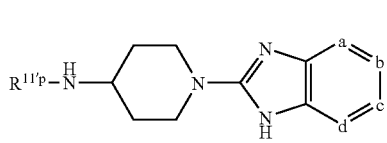

(V-b")

(wherein a, b, c, d and $R^{11p}$ are as defined hereinbefore), followed by optional removal of the protecting group to produce a compound represented by the general formula (I-b"):

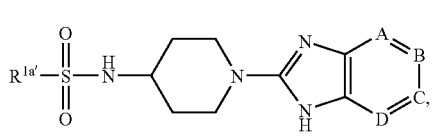

(I-b")

wherein A, B, C, D and $R^{1a'}$ are as defined hereinbefore.

This production process constitutes a production process for the compounds represented by the general formula (I) wherein E is represented by either of the following formulae (E1b):

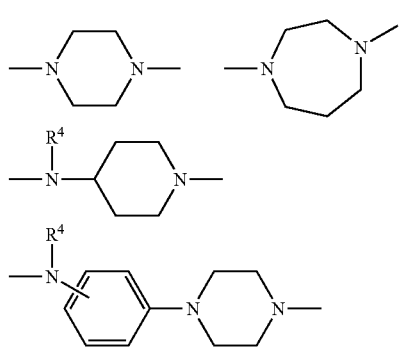

(E1b)

-continued

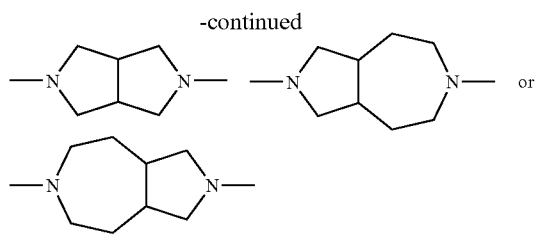

(wherein $R^4$ is as defined hereinbefore), namely the production process for the compound represented by the general formula (I-b), (I-b') or (I-b").

The leaving group represented by $L^1$ is exemplified by halogen atoms, such as chlorine, bromine or iodine, etc., organic sulfonyl groups, such as methanesulfonyl, ethanesulfonyl and benzenesulfonyl, etc., or organic sulfonyloxy groups, such as methanesulfonyloxy, trifluoromethanesulfonyloxy and p-toluenesulfonyloxy, etc.

As an imino-protecting group represented by $P^2$ includes, for example, the imino-protecting group as described in the above-described Production Process 1.

The reaction of the compound represented by the general formula (VII) with the compound represented by the general formula (VIII) is carried out while using 1 mole to excessive moles, preferably 1 mole to 1.5 moles, of the compound (VIII) against 1 mole of the compound (VII). The reaction is ordinarily effected in an inert solvent, and preferable examples of the inert solvent include methylene chloride, chloroform, tetrahydrofuran, dioxane, dimethylformamide, N-methylpyrrolidone and dimethylsulfoxide, etc. or solvent mixtures thereof, etc.

The above-described reaction is preferably carried out in the presence of a base, and as the said base, for example, use can be made, for example, of organic bases, such as triethylamine, diisopropylethylamine, pyridine and 4-dimethylaminopyridine, etc., or inorganic bases, such as sodium hydrogencarbonate, sodium carbonate, potassium carbonate, cesium carbonate, sodium hydroxide and potassium hydroxide, etc.

The amount of the said base used generally is in ratios of 1 mole to excessive moles, preferably 1 to 5 moles, against 1 mole of the compound represented by the general formula (VII).

The reaction temperature generally ranges from 0° C. to 200° C., preferably from 20° C. to 150° C.

The reaction time ordinarily ranges from 5 min. to 7 days, preferably from 30 min. to 24 hrs.

After completion of the reaction, a conventional treatment can be conducted to give the compound represented by the general formula (V-b) in the form of a crude product.

The compound represented by the general formula (V-b) wherein i) $R^{11p}$ is a group represented by the formula (bb1), after being purified in accordance with a conventional method or directly without being purified, can be optionally subjected to a suitable combination of the removal reactions for the protective groups for amino, imino, hydroxy, carboxy and carbonyl groups to produce the compound of the general formula (I-b).

The removal of the protecting groups, post treatment and the like can be conducted into practice in accordance with methods similar to those described in the above Production Process 1.

The compound represented by the general formula (V-b) wherein ii) $R^{11p}$ is an amino- or imino-protecting group, after removal of the said protective group for an amino or imino group, can be reacted with the compound represented by the general formula (VI) in the presence of a base, followed by a conventional treatment, to give the compound of the general formula (V-b') in the form of a crude product. The thus-obtained compound represented by the general formula (V-b'), after being purified in accordance with a conventional method or directly without being purified, can be optionally subjected to a suitable combination of the removal reactions for the protective groups for amino, imino, hydroxy, carboxy and carbonyl groups to produce the compound of the general formula (I-b').

The reaction step for the compound represented by the general formula (VI), removal of the protective groups, post treatment and the like can be conducted into practice in accordance with methods similar to those described in the above Production Process 1.

The compound represented by the general formula (V-b) wherein iii) $R^{11p}$ is an azide group, after reduction of the said azide group, can be reacted with the compound represented by the general formula (VI) in the presence of a base, followed by a conventional treatment, to give the compound of the general formula (V-b") in the form of a crude product. The thus-obtained compound represented by the general formula (V-b") can be treated in the same manner as described above for the case ii) to produce the compound of the general formula (I-b").

The step for reduction of the azide group, step for reaction with the compound represented by the general formula (VI), removal of the protective groups, post treatment and the like can be conducted into practice in accordance with methods similar to those described in the above Production Process 1.

Production Process 3

A compound represented by the general formula (IX):

(wherein $R^{12p}$ is a group represented by the following formula (bb2):

(wherein $R^{1p}$ means a lower alkyl group or an aryl group, said aryl group may optionally having a substituent(s) selected from the group consisting of a halogen atom, a cyano group, a lower alkyl group, a halo-lower alkyl group, a lower alkoxy group, a halo-lower alkoxy group, a lower alkylamino group, a di-lower alkylamino group, a lower alkanoyl group and an aryl group, an optionally protected hydroxy-lower alkyl and an optionally protected hydroxy groups, or means a lower alkylene group which is linked to arbitrary, linkable position(s) of $E^b$), or means an amino- or imino-protecting group, or means an azide group when E is a group represented by the following formula (E1b-1):

(E is as defined hereinbefore), or a salt thereof, is reacted with a compound represented by the general formula (III):

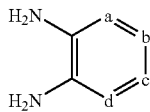
(III)

(wherein a, b, c and d are as defined hereinbefore) to give a compound represented by the general formula (V):

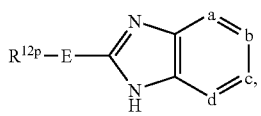
(V)

wherein a, b, c, d, E and $R^{12p}$ are as defined hereinbefore.

i) When $R^{12p}$ is a group represented by the formula (bb2), the protective group in the said compound (V) is optionally removed to produce a compound represented by the general formula (I):

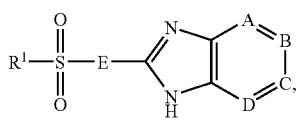
(I)

wherein A, B, C, D, E and $R^1$ are as defined hereinbefore; or ii) when $R^{12p}$ is the protective group in the compound represented by the general formula (V), an amino- or imino-protecting group is optionally removed, and then the said compound is reacted with a compound represented by the general formula (VI):

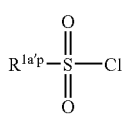
(VI)

to give a compound represented by the general formula (V'):

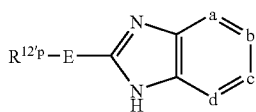
(V')

(wherein $R^{12p}$ is a group represented by the following formula (bb1):

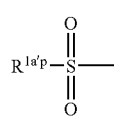
(bb1')

(wherein $R^{1a'p}$ is as defined hereinbefore); a, b, c, d and E are as defined hereinbefore), followed by optional removal of the protective group to thereby produce a compound represented by the general formula (I'):

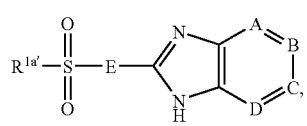
(I')

wherein A, B, C, D, E and $R^{1a'}$ are as defined hereinbefore; or iii) When $R^{12p}$ is an azide group in the compound represented by the general formula (V), the azide group is reduced, and then the said compound is reacted with a compound represented by the general formula (VI):

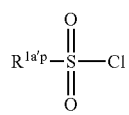
(VI)

(wherein $R^{1a'p}$ is as defined hereinbefore) to give a compound represented by the general formula (V"):

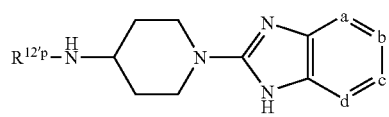
(V")

(wherein a, b, c, d and $R^{12p}$ are as defined hereinbefore), followed by optional removal of the protective groups for the compound (V") to thereby produce a compound represented by the general formula (I-b"):

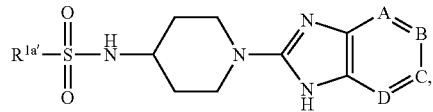
(I-b")

wherein A, B, C, D and $R^{1a'}$ are as defined hereinbefore.

The reaction of the compound represented by the general formula (IX) with the compound represented by the general formula (III) is generally carried out while using 0.5 mole to 5 moles, preferably 0.7 mole to 3 moles, of the compound (III) against 1 mole of the compound (IX).

The reaction is ordinarily effected in non-solvent or conducted in an inert solvent, and preferable examples of the said inert solvent include, for example, benzene, toluene, xylene, methylene chloride, chloroform and hexane, etc. or solvent mixtures thereof, etc.

The reaction temperature generally ranges from −20° C. to the boiling point of the solvent used, preferably from 20° C. to 200° C.

The reaction time ordinarily ranges from 30 min. to 7 days, preferably from 3 hrs. to 3 days.

The above-described reaction is preferably carried out in the presence of a Lewis acid, and the Lewis acid is exemplified by zinc dichloride, titanium tetrachloride, scandium trifluoromethanesulfonate, ytterbium trifluoromethanesulfonate and lanthanum trifluoromethanesulfonate, etc.

The amount of the said Lewis acid used generally ranges from 10 mole % to 200 mole %, preferably from 20 mole % to 100 mole %, against 1 mole of the compound represented by the general formula (IX).

When the reaction is effected in the presence of a Lewis acid, it is preferably carried out in a non-solvent or performed for example in methylene chloride, chloroform, benzene, toluene and xylene, etc. or solvent mixtures thereof, etc.

The reaction temperature generally ranges from 0° C. to the boiling point of the solvent used, preferably from room temperature to 150° C.

The reaction time ordinarily ranges from 1 hr. to 7 days, preferably from 12 hrs. to 3 days.

i) The compound represented by the general formula (V) wherein $R^{12p}$ is a group represented by the formula (bb2), after being purified in accordance with a conventional method or directly without being purified, can be optionally subjected to a suitable combination of the removal reactions for an amino- or imino-protecting group, a hydroxy-protecting group, a carboxy-protecting group and carbonyl-protecting group to produce the compound of the general formula (I).

The removal of the protecting groups, post treatment and the like can be conducted into practice in accordance with methods similar to those described in the above-described Production Process 1.

ii) The compound represented by the general formula (V) wherein $R^{12p}$ is an amino- or imino-protecting group, after removal of the amino- or imino-protecting group, can be reacted with the compound represented by the general formula (VI) in the presence of a base, followed by a conventional treatment, to give the compound of the general formula (V') in the form of a crude product. The thus-obtained compound represented by the general formula (V'), after being purified in accordance with a conventional method or directly without being purified, can be optionally subjected to a suitable combination of the removal reactions for an amino- or imino-protecting group, a hydroxy-protecting group, a carboxy-protecting group and a carbonyl-protecting group to produce the compound of the general formula (I').

The reaction step for the compound represented by the general formula (VI), removal of the protective groups, post treatment and the like can be conducted into practice in accordance with methods similar to those described in the above Production Process 1.

iii) The compound represented by the general formula (V) wherein $R^{12p}$ is an azide group, after reduction of the azide group, can be reacted with the compound represented by the general formula (VI) in the presence of a base, followed by a conventional treatment after completion of the reaction, to give the compound of the general formula (V''') in the form of a crude product. The thus-obtained compound represented by the general formula (V''') can be treated in the same manner as described above for the case ii) to produce the compound of the general formula (I-b'').

The step for reduction of the azide group, step for the subsequent reaction with the compound represented by the general formula (VI), removal of the protective groups, post treatment and the like can be conducted into practice in accordance with methods similar to those described in the above Production Process 1.

The compounds represented by the general formulae (I), (I'), (I-a), (I-a'), (I-a''), (I-b), (I-b') or (I-b'') can be easily isolated and purified by a conventional separation technique. Such technique can be exemplified by solvent extraction, recrystallization, column chromatography and collective thin-layer chromatography, etc.

These compounds can be converted to their pharmaceutically acceptable salts by a conventional method, and the reverse conversion from such salts to the free compounds can be carried out in accordance with a conventional method.

The compounds represented by the general formulae (II), (III), (VI), (VII), (VIII) or (IX), for example, are commercially available, or can be produced by a suitable combination of the known methods or methods similar thereto, or the methods as described in Examples and Reference Examples hereof, etc.

The "salts" of the compounds represented by the general formulae (III), (VIII) or (IX) mean any conventional ones as used in the field of organic chemistry, and may be exemplified by base-addition salts of a carboxy group when they have such carboxy group, or acid-addition salts of an amino or basic heterocyclic group when they have such amino or basic heterocyclic group.

The said base-addition salts include, for example, alkali metal salts, such as sodium and potassium salts, etc.; alkaline earth metal salts, such as calcium and magnesium salts, etc.; ammonium salts; organic amine salts, such as trimethylamine, triethylamine, dicyclohexylamine, ethanolamine, diethanolamine, triethanolamine, procaine and N,N'-dibenzylethylenediamine salts, etc.; and the like.

The said acid-addition salts include, for example, inorganic acid salts, such hydrochlorides, sulfates, phosphates and perchlorates, etc.; organic acid salts, such as maleates, fumarates, tartarates, citrates, ascorbates and trifluoroacetates, etc.; and sulfonates, such as methanesulfonates, isethionates, benzenesulfonates and p-toluenesulfonates, etc.; and the like. The utility of the compounds of the present invention as a drug is proved by for example, the following pharmacological tests.

PHARMACOLOGIC TEST EXAMPLES

Pharmacological Test Example 1

NPY Binding Inhibition Test

The cDNA sequence (refer to the specification of WO 96/16542) encoding human NPY Y5 receptor was cloned into the expression vectors, pcDNA3, pRc/RSV (supplied by Invitrogen Co.) and pCI-neo (supplied by Promega Co.). The resultant expression vectors were transfected into the host cells, COS-7, CHO and LM(tk−) (American Type Culture Collection) using the cationic lipid method (refer to Proceedings of the National Academy of Sciences of the United States of America, vol. 84, pp. 7413 (1987)) to give NPY Y5 receptor expression cells. A membrane sample prepared from the NPY Y5 receptor expressed cells was incubated together with a test compound and 20,000 cpm of [$^{125}$I]peptide YY (supplied by NEN Co.) in an assay buffer (25 mM Tris buffer, pH 7.4, containing 10 mM of magnesium chloride, 1 mM of phenylmethylsulfonyl fluoride, 0.1% bacitracin and 0.5% bovine serum albumin) at 25° C. for 2 hours, followed by filtration through glassfilter GF/C. After washing with 5 mM Tris buffer (pH7.4) containing 0.3% BSA, radioactivity of the cake on the filter was measured. Non-specific binding was measured in the presence of 1 µM of peptide YY, and a 50% Inhibition Concentration ($IC_{50}$ value) of the test compound against specific peptide YY binding was determined (refer to Endocrinology, vol. 131, pp. 2090 (1992)). The results are shown in Table 1.

TABLE 1

| Compounds | $IC_{50}$(nM) |
|---|---|
| Example 3 | 0.67 |
| Example 4 | 1.4 |
| Example 7 | 1.2 |
| Example 9 | 1.6 |
| Example 17 | 1.5 |
| Example 22 | 1.7 |

As is obvious from the above, the compounds of the present invention inhibited potently the binding of peptide YY (NPY homologue) to the NPY Y5 receptor.

Pharmacological Test Example 2

Antagonistic Effect on D-Trp$^{34}$ NPY-Induced Feeding Behavior

A chronic guide cannula (26 guage, length 11 mm) is inserted in a stereotaxic manner into the third cerebral ventricle of male SD rats (7-8 weeks aged, 200-300 g weighed) anesthetized with ketamine/xylazine (74 and 11 mg/kg given intraperitoneally in a single dose) and fixed with a dental resin. The top of the guide-cannula is located 2.2 mm behind bregma and 8 mm depth from the skull surface on the median line. After the recovery period is allowed for about one week, D-Trp$^{34}$ NPY (NPY homologue, 1 µg/0.4 µL/head, synthetic cerebrospinal fluid containing 0.05% bovine serum albumin) is injected into the third cerebral ventricle. A test compound suspended in a 0.5% aqueous solution of methylcellulose is administered orally 2 hours before the administration of D-Trp$^{34}$ NPY, and the food consumption is measured 2 hours after the administration of D-Trp$^{34}$ NPY.

Pharmacological Test Example 3

Pharmacokinetic Test

A test compound is administered orally or intravenously to male SD rats (7-10 weeks aged, 200-400 g weighed) which abstained from overnight. About 100 µL of blood is collected from the tail vein at predetermined time, using a heparinized capillary. The blood is centrifuged (at 4° C., 6,000 rpm, for 10 min) to obtain the plasma, to which 3-fold amount of ethanol (containing the internal standard substance) is added, followed by stirring, standing at −20° C. for 20 minutes and centrifugation (at 4° C., 10,000 rpm, for 10 min). The supernatant is analyzed by LC/MS/MS to thereby measure the plasma level based on the relative calibration curve method.

Pharmacological Test Example 4

Brain/Cerebrospinal Fluid Transport Test

A test compound is administered orally or intravenously to male SD rats (7-10 weeks aged, 200-400 g weighed), and a whole-blood is collected from the abdominal aorta of the rats anaesthetized with ether at predetermined time, using a heparin-treated syringe. The head skin is cut open, and a dental 30 G needle is inserted between the cervical vertebrae and then furthermore inserted into the cavum subarachnoideale. The cerebrospinal fluid in the volume of 50-100 µL is collected into a syringe of a 1-mL capacity through a tube connected to the dental 30 G needle, followed by extraction of brain. The plasma obtained by centrifugation (at 4° C., 6,000 rpm, for 10 min) of the blood sample is admixed with a 3-fold amount of ethanol (containing the internal standard substance), followed by stirring, while the brain sample is homogenized after addition of 2 mL of water, and an aliquot of the homogenate is admixed with a 3-fold amount of ethanol (containing the internal standard substance), followed by stirring. The above samples are left on standing at −20° C. for 20 minutes and centrifuged (at 4° C., 12,000 rpm, for 10 min), and the supernatants are analyzed by LC/MS/MS to thereby determine the concentration of the test compound in the plasma, brain and cerebrospinal fluid based on the relative calibration curve method.

The compounds represented by the general formula (I) can be administered orally or parenterally, and can be formulated into the dosage forms suited for such administration to thereby be used as an agent of treatment of cardiovascular disorders, such as angina, acute or congestive heart failure, myocardial infarction, hypertension, nephropathy, electrolyte abnormality, vasospasm and artherosclerosis, etc.; central nervous system diseases, such as bulimia, depression, anxiety, seizure, epilepsy, dementia, pain, alcoholism, drug withdrawal, circadian rhythm disorders, schizophrenia, memory impairment, sleep disorders and cognitive impairment, etc.; metabolic diseases, such as obesity, diabetes, hormone abnormality, hypercholesterolemia, hyperlipidemia, gout and fatty liver, etc.; genital or reproductive disorders, such as infertility, preterm labor and sexual dysfunction, etc.; gastro-intestinal disorders; respiratory disorders; inflammatory diseases; or glaucoma; and the like, as well as atherosclerosis; hypogonadism; hyperandrogenism; polycystic ovary syndrome; hirsutism; gastro-intestinal motility disorder; obesity-related gastro-esophageal reflux; obesity-hypoventilation (Pickwickian syndrome); sleep apnea; inflammation; systemic inflammation of the vasculature; osteoarthritis; insulin resistance; bronchoconstriction; alcohol preference, metabolic syndrome (syndrome X); Alzheimer's disease; cardiac hypertrophy; left ventricular hypertrophy; hypertriglyceridemia; low HDL cholesterol; cardiovascular disorders, such as coronary heart disease (CHD), cerebrovascular disease, stroke, peripheral vascular diseases and sudden death, etc.; gallbladder diseases; cancers (breast cancer, endometrial cancer, colon cancer); breathlessness; hyperuricemia; impaired fertility; low back pain; increased anesthetic risk; renal system diseases; renal abnormalities, such as dysfunction in body fluid flow, abnormalities of material transportation and renal failure; shock; arrhythmia; symptoms related to surge in sympathomimetic activity during or after operation on coronary artery or gastrointestinal tracts; diseases related to brain or central nervous system, such as cerebral infarction, neurodegeneration or cerebral stroke, cerebrovascular spasm or cerebral hemorrhage; symptoms related to pain or nociception; diseases related to abnormalities in gastrointestinal motility or secretion, such as various ileuses, urinary incontinence and Crohn's disease, etc.; eating disorders, such as anorexia and bulimia, etc.; inflammatory symptoms or diseases; asthma; bronchiole constriction, or diseases related to abnormal secretion of hormones, such as lutenizing hormone, growth hormone, insulin and luteotropic hormone, etc The compounds of the present invention, in their clinical application and utilization, can also be administered after being formulated in a variety of dosage forms by admixing with pharmaceutically acceptable additives to fit in with the forms of administration. As the additives to be used in such occasions, a variety of additives being conventionally used in the filed of pharmaceutical preparations can be utilized, and include, for example, gelatin, lactose, sucrose, titanium oxide, starch, crystalline cellulose, hydroxypropyl methylcellulose, carboxymethylcellulose, corn starch, microcrystalline wax, petrolatum album, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened caster oil, polyvinylpyrrolidone, magnesium stearate, light anhydrous silicic acid, talc, vegetable oils, benzylalcohol, gum arabic, propylene glycol, polyalkylene glycol, cyclodextrins or hydroxypropyl cyclodextrins, etc.

The dosage form, namely the pharmaceutical preparation form, into which a mixture of these additives together with the compounds of the present invention is formulated and processed, is exemplified by solid dosage forms, such as tablets, capsules, granules, powders or suppositories, etc.; or liquid dosage forms, such as syrups, elixirs or injections, etc., and these can be manufactured in accordance with methods or processes conventionally known in the field of the pharmaceutical formulation. The liquid dosage form may be processed into the ones which are to be dissolved or suspended in water or other suitable media on the occasion of application or use. In particular, furthermore, the injectable solution may be dissolved or suspended in physiological saline or glucose solution, as the case may be, and incorporated additionally with a buffer or preservative.

The compounds of the present invention are effective to humans or mammals other than humans who are in need of treatment with the said compounds. The said mammals preferably include humans, which may be male or female. The mammals other than humans may be exemplified by companion animals such as dogs and cats. The compounds of the present invention are effective for obesity or obesity associated diseases of such dogs and cats, etc. It can be easily determined by ordinarily skilled physicians, veterinarians or clinicians whether or not the treatment with the said compounds is required.

In using the compounds of the present invention for the clinical purposes, their dosage and frequency of administration vary depending upon the sex, age, body weight, and the degree of seriousness of conditions of patients, and the mode and range of the intended treatment effect, and they generally are desirably administered to human adults orally in the daily dose of 0.01 to 100 mg/kg, preferably 0.03 to 1 mg/kg once or as divided in several times, or parenterally in the daily dose of 0.001 to 10 mg/kg, preferably 0.001 to 0.1 mg/kg, more preferably 0.01 to 0.1 mg/kg, once or as divided in several times.

Ordinary skilled physicians, veterinarians or clinicians can easily determine, and dispense or prescribe the effective amount of a drug to prevent, suppress or arrest the progress of diseases.

Such dosage forms can be incorporated with the compounds of the present invention in the ratios of 1.0 to 100% by weight, preferably 1.0 to 60% by weight, on the basis of the total weight of the pharmaceutical preparation, and may contain therapeutically effective other compounds.

The compounds of the present invention can be used in combination with other effective drugs for the treatment of metabolic disorders and/or eating disorders. Individual ingredients of such combinations can be administered to patients during the treatment period on separately different occasions or simultaneously in divided or single dosage forms. Consequently, the present invention should be construed to encompass all the regimens of the simultaneous or intermittent administration, and the administration as mentioned in the present invention should be understood to be as such accordingly. The scope of combinations of the compounds of the present invention with other drugs useful for the treatment of metabolic disorders and/or eating disorders in principle encompasses their combinations with all and any drug preparations useful for the treatment of metabolic disorders and/or eating disorders.

Diabetes is caused by multiple factors and is most simply characterized by elevated levels of plasma glucose (hyperglycemia) in the fasting state. There are two generally recognized forms of diabetes: type 1 diabetes, or insulin-dependent diabetes mellitus (IDDM), in which patients produce little or no insulin, the hormone which regulates glucose utilization, and type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

The persistent or uncontrolled hyperglycemia that occurs in diabetics is associated with increased morbidity and premature mortality. Type 2 diabetics are at increased risk of developing cardiovascular complications, e.g., atherosclerosis, coronary heart disease, stroke, peripheral vascular disease, hypertension, nephropathy, neuropathy and retinopathy.

Non-insulin dependent diabetes is also associated with cardiac hypertrophy, in particular left ventricular hypertrophy (Devereux, R. B., Circulation, 101:2271-2276 (2000)). Cardiac hypertrophy, such as left ventricular hypertrophy, is due to the response of the heart to chronic pressure or volume overload. Left ventricular hypertrophy (LVH) is characterized by thickening of the left ventricular wall, including increased left ventricular mass and increased left ventricular wall thickness, and is defined as a left ventricular mass index exceeding 131 g/m2 of the body surface area in men, and 100 g/m2 in women (Savage et al., The Framingham Study, Circulation, 75 (1 Pt 2): 26-33 (1987).

Left ventricular hypertrophy is independently associated with increased incidence of cardiovascular disease, such as congestive heart failure, ischaemic heart disease, cardiovascular and all-cause mortality, sudden death, and stroke. Regression of left ventricular hypertrophy has been associated with a reduction in cardiovascular risk. It has also been found that the incidence of morbid events in patients with progression of left ventricular hypertrophy is greater than in patients with regression of left ventricular hypertrophy.

Current treatments for hypertrophy include non-pharmacological interventions, such as weight reduction, sodium restriction, and aerobic physical exercise can reduce left ventricular mass (Ghali, J. K. et al., American Journal of Geriatric Cardiology, 6:38-49 (1997).

Many patients who have insulin resistance but have not yet developed type 2 diabetes are also at a risk of developing metabolic syndrome, also referred to as syndrome X, insulin resistance syndrome, or plurimetabolic syndrome. The period of 5 to 10 years preceding the development of impaired glucose tolerance is associated with a number of hormonal imbalances, which give rise to an enlargement of visceral fat mass, hypertension, insulin resistance, and hyperlipidemia (Bjornstop, P., Current Topics in Diabetes Research, eds. Belfore, F., Bergman, R. N., and Molinath, G. M., Front Diabetes, Basel, Karger, 12:182-192 (1993)). Similarly, metabolic syndrome is characterized by insulin resistance, along with abdominal obesity, hyperinsulinemia, high blood pressure, syndrome X, low HDL and high VLDL. Although the causal relationship between the various components of metabolic syndrome remains to be confirmed, insulin resistance appears to play an important role (Requen, G. M., et al., N. Eng. J. Med. 334:374-381 (1996); Despres, J-P., et al., N. Engl. J. Med. 334:952-957 (1996); Wajchenberg, B. L., et al., Diabetes/Metabolism Rev. 10:19-29 (1994)). Metabolic syndrome patients, whether or not they develop overt diabetes mellitus, are at increased risk of developing the cardiovascular complications listed above. Associations have also been found between left ventricular hypertrophy and metabolic syndrome (Marcus, R. et al. Circulation, 90:928-936 (1994); Lind, L. et al., J Hypertens. 13:433-38 (1995); Paolisso, G et al., Am J Hypertens., 10:1250-1256 (1997).

Type 2 diabetes is treated with a variety of therapeutic agents including insulin sensitizers, such as PPARγ agonists, such as glitazones; biguanides; protein tyrosine phosphatase-1B inhibitors; dipeptidyl peptidase IV inhibitors; insulin; insulin mimetics; sulfonylureas; meglitinides; α-glucoside hydrolase inhibitors; and α-amylase inhibitors.

Increasing the plasma level of insulin by administration of sulfonylureas (e.g. tolbutamide and glipizide) or meglitinides, which stimulate the pancreatic β-cells to secrete more insulin, and/or by injection of insulin when sulfonylureas or meglitinides become ineffective, can result in insulin concentrations high enough to stimulate insulin-resistant tissues. However, dangerously low levels of plasma glucose can result, and increasing insulin resistance due to the even higher plasma insulin levels can occur. The biguanides increase insulin sensitivity resulting in some correction of hyperglycemia. Alpha-amylase inhibitors inhibit the enzymatic degradation of starch or glycogen into maltose, which also reduces the amounts of bioavailable sugars. Metformin monotherapy is often used for treating type 2 diabetic patients who are also obese and/or dyslipidemic. Lack of appropriate response to metformin is often followed by treatment with sulfonylureas, thiazolidinediones, insulin, or alpha glucosidase inhibitors. However, the two biguanides, phenformin and metformin, can also induce lactic acidosis and nausea/diarrhea, respectively. Alpha glucosidase inhibitors, such as acarbose, work by delaying absorption of glucose in the intestine.

The glitazones, also known as thiazolidinediones (i.e. 5-benzylthiazolidine-2,4-diones), are a more recently described class of compounds with potential for a novel mode of action in ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. Newer PPAR agonists that are being developed for treatment of Type 2 diabetes and/or dyslipidemia are agonists of one or more of the PPAR alpha, gamma and delta subtypes.

However, treatment of diabetes with PPARγ agonists has been associated with cardiac hypertrophy, or an increase in heart weight. Recent labeling revisions for Avandia (rosiglitazone maleate), a PPARγ agonist, indicate that patients may experience fluid accumulation and volume-related events such as edema and congestive heart failure. Cardiac hypertrophy related to PPARγ agonist treatment is typically treated by withdrawing PPAR treatment.

Treatment of type 2 diabetes also typically includes physical exercise, weight control and dieting. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. However, weight reduction and increased exercise are difficult for most people with diabetes.

Abnormal glucose homeostasis is also associated both directly and indirectly with obesity, hypertension and alterations in lipid, lipoprotein and apolipoprotein metabolism. Obesity increases the likelihood of insulin resistance, and increases the likelihood that the resulting insulin resistance will increase with increasing body weight. Therefore, therapeutic control of glucose homeostasis, lipid metabolism, obesity and hypertension are critically important in the clinical management and treatment of diabetes mellitus.

Obesity, which can be defined as a body weight more than 20% above the ideal body weight, is a major health concern in Western societies. It is estimated that about one third of adults are overweight or obese. Obesity is the result of a positive energy balance, as a consequence of increased ratio of caloric intake to energy expenditure. The molecular factors regulating food intake and body weight balance are incompletely understood. [B. Staels et al., J. Biol. Chem. 270(27), 15958 (1995); F. Lonnquist et al., Nature Medicine 1(9), 950 (1995)]. Although the genetic and/or environmental factors leading to obesity are poorly understood, several genetic factors have been identified.

Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include type 2 diabetes mellitus, hypertension, elevated plasma insulin concentrations, insulin resistance, dyslipidemias, hyperlipidemia, endometrial, breast, prostate, kidney and colon cancer, osteoarthritis; respiratory complications, such as obstructive sleep apnea, gallstones, arteriosclerosis, heart disease, abnormal heart rhythms, and heart arrythmias (Kopelman, P. G., Nature 404, 635-643 (2000)). Obesity is also associated with metabolic syndrome, cardiac hypertrophy, in particular left ventricular hypertrophy, premature death, and with a significant increase in mortality and morbidity from stroke, myocardial infarction, congestive heart failure, coronary heart disease, and sudden death.

Abdominal obesity has been linked with a much higher risk of coronary artery disease, and with three of its major risk factors: high blood pressure, diabetes that starts in adulthood, and high levels of fats (lipids) in the blood. Losing weight dramatically reduces these risks. Abdominal obesity is further closely associated with glucose intolerance, hyperinsulinemia, hypertriglyceridemia, and other disorders associated with metabolic syndrome (syndrome X), such as raised high blood pressure, decreased levels of high density lipoproteins (HDL) and increased levels of very low density lipoproteins (VLDL) (Montague et al., Diabetes, 2000, 49: 883-888).

Obesity and obesity-related disorders, such as diabetes, are often treated by encouraging patients to lose weight by reducing their food intake or by increasing their exercise level, thereby increasing their energy output. A sustained weight loss of 5% to 10% of body weight has been shown to improve the comorbidities associated with obesity, such as diabetes, and can lead to improvement of obesity-related disorders such as diabetes, left ventricular hypertrophy, osteoarthritis, and pulmonary and cardiac dysfunction.

Weight loss drugs used for the treatment of obesity include orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5). However, the side effects of these drugs and anti-obesity agents may limit their use. Dexfenfluramine was withdrawn from the market because of suspected heart valvulopathy; orlistat is limited by gastrointestinal side effects; and the use of sibutramine is limited by its cardiovascular side effects which have led to reports of deaths and its withdrawal from the market in Italy.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). The compositions of the present invention are useful for treating both Type 1 and Type 2 diabetes. The compositions are especially effective for treating Type 2 diabetes. The compositions of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be decreasing insulin levels in a subject with elevated insulin levels. Another outcome of treatment is decreasing plasma triglycerides in a subject with elevated plasma triglycerides. Another outcome of treatment is decreasing LDL cholesterol in a subject with high LDL cholesterol levels. Another outcome of treatment is increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin.

Prevention of diabetes mellitus refers to the administration of a compound or combination of the present invention to prevent the onset of diabetes in a subject in need thereof.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "left venticular hypertrophy" (LVH) as used herein includes three patterns of left ventricular hypertrophy that have been identified based on left ventricular mass index (LVMI=left ventricular mass in grams divided by body surface area in meters2) and relative wall thickness (RWT=2× posterior wall thickness/left ventricular end diastolic diameter). Concentric LVH is typically exemplified by a left ventricular mass index of 144 and a relative wall thickness of 0.52; eccentric LVH is typically exemplified by a left ventricular mass index of 136 and a relative wall thickness of 0.38; and concentric left ventricular remodeling which is typically exemplified by a LVMI of 93 and a relative wall thickness of 0.49. Normal LVMI are typically 85 and normal RWT approximately 0.36. Patients with concentric left ventricular (LV) remodeling have a cardiovascular risk intermediate between those with normal left ventricular structure and those with left ventricular hypertrophy.

One outcome of treatment of diabetes while minimizing cardiac hypertrophy, or left ventricular hypertrophy, may be a decrease in ventricular mass. Another outcome of treatment of diabetes while minimizing cardiac hypertrophy or left ventricular hypertrophy may be a decrease in the rate of increase of ventricular mass. Another outcome of treatment of diabetes while minimizing cardiac hypertrophy or left ventricular hypertrophy may be a decrease in ventricular wall thickness. Another outcome of treatment of diabetes while minimizing cardiac hypertrophy of left ventricular hypertrophy may be the decrease in the rate of increase in ventricular wall thickness.

The term "obesity" as used herein is a condition in which there is an excess of body fat. The operational definition of obesity is based on the Body Mass Index (BMI), which is calculated as body weight per height in meters squared (kg/m$^2$). An "obese subject" is an otherwise healthy subject with a Body Mass Index (BMI) greater than or equal to 30 kg/m2 or a subject with at least one co-morbidity with a BMI greater than or equal to 27 kg/m$^2$. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-diabetic agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Circadian rhythms affect a variety of physiological parameters: rest-activity, sleep-wake cycles, body temperature, rhythms in hormone levels, oscillations in general physiology and the like. When these parameters are out of synchrony with the daily clock, a circadian rhythm imbalance occurs which can affect physiology, performance on a variety of tasks and one's emotional well being. The present invention is useful, for example, in the prevention or treatment of conditions associated with circadian rhythmicity as well as mental and physical disorders associated with travel across time zones and with rotating shift-work schedules.

In another embodiment, the present invention provides a method for the prevention or treatment of a circadian rhythm disorder in a mammal, including time-zone change syndrome, shift-work sleep disorder, delayed sleep-phase syndrome, advanced sleep-phase syndrome, and non-24-hour sleep-wake disorder.

In another embodiment, the present invention provides a method for shortening the time of re-entrainment (return to normal entrainment of the circadian rhythms; synchronized to the environmental light-dark cycle) in a subject following a shift in the sleep-wake cycle.

In another embodiment, the present invention provides a method for alleviating the effects of jet lag in a traveler. The purpose of this embodiment is to assist the body to adjust physiologically to the changes in sleep and feeding patterns when crossing several time zones.

In another more preferred embodiment, the present invention provides a method for resetting the internal circadian clock in a subject to match the subject's current activity/sleep cycle. For example shift workers changing from a day to a night shift or vice versa.

The present invention provides a method for enhancing or improving sleep quality by increasing sleep efficiency and augmenting sleep maintenance. In addition, the present invention provides a method for preventing and treating sleep disorders and sleep disturbances. The present invention further provides a pharmaceutical composition for enhancing or improving sleep quality and increasing sleep efficiency and sleep maintenance. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The following outcomes in a subject which are provided by the present invention may be correlated to enhancement in sleep quality: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance. Secondary outcomes which may be provided by the present invention include enhanced cognitive function and increased memory retention. A "method for enhancing the quality of sleep" refers to a method that results in outcomes in a subject which may be correlated to enhancement in sleep quality, including, but not limited to, the outcomes correlated to enhancement of sleep quality as defined above.

The present invention is further useful for the prevention and treatment of sleep disorders and sleep disturbances including sleep problems associated with insomnia, hypersomnia, sleep apnea, narcolepsy, nocturnal myoclonus, REM sleep interruptions, jet-lag, shift workers' sleep disturbances, dysomnias, night terror, night eating syndrome, insomnias associated with depression or with emotional/mood disorders, dysfunctions associated with sleep (parasomnias), as well as sleep walking and enuresis, as well as sleep disorders which accompany aging. Sleep disorders and sleep disturbances are generally characterized by difficulty in initiating or maintaining sleep or in obtaining restful or enough sleep.

In addition, certain drugs may also cause reductions in REM sleep as a side effect and the present invention may be used to correct those types of sleeping disorders as well. The present invention would also be of benefit in the treatment of syndromes such as fibromyalgia which are manifested by non-restorative sleep and muscle pain or sleep apnea which is associated with respiratory disturbances during sleep. It will be clear to one skilled in the art that the present invention is not limited to just sleep disorders and sleep disturbances, but is applicable to a wide variety of conditions which result from a diminished quality of sleep.

The present invention is also concerned with treatment and prevention of these conditions, combinations, and compositions thereof, for the manufacture of a medicament useful for treating or preventing these conditions.

In the present invention, it is preferred that the subject mammal is a human. Although the present invention is applicable both old and young people, it may find greater application in elderly people. Further, although the invention may be employed to enhance the sleep of healthy people, it may be especially beneficial for enhancing the sleep quality of people suffering from sleep disorders or sleep disturbances.

The compositions of the present invention may be used in combination with other drugs that may also be useful in the treatment, prevention, or control of disorders, such as hypertension, hypertension associated with obesity, hypertension-related disorders, cardiac hypertrophy, left ventricular hypertrophy, and metabolic syndrome, obesity and obesity-related disorders, for which compounds comprising the compositions are useful. Such other drugs may be administered, by a route and in an amount commonly used therefore, contemporaneously or sequentially with a composition of the present invention. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that contain one or more other active ingredients, in addition to a composition of the present invention.

Examples of other active ingredients that may be administered in combination with a composition of the present invention, and either administered separately or in the same pharmaceutical composition, include, but are not limited to: (a) (i) PPARγ agonists, such as glitazones (e.g., ciglitazone, darglitazone, englitazone, isaglitazone (MCC-555), pioglitazone, rosiglitazone, troglitazone, BRL49653, CLX-0921, 5-BTZD, etc.), and GW-0207, LG-100641 and LY-300512, etc., (ii) biguanides, such as buformin, metformin and phenformin, etc., (iii) protein tyrosine phosphatase-1B (PTP-1B) inhibitors, (iv) sulfonylureas, such as acetohexamide, chlorpropamide, diabinese, glibenclamide, glipizide, glyburide, glimepiride, gliclazide, glipentide, gliquidone, glisolamide, tolazamide and tolbutamide, etc., (v) meglitinides, such as regaglinide and nateglinide, etc., (vi) alpha-glucoside hydrase inhibitors, such as acarbose, adiposine, camiglibose, emiglitate, miglitol, voglibose, pradimicin-Q, salbostatin, CKD-711, MDL-25,637, MDL-73,945 and MOR 14, etc., (vii) alpha-amylase inhibitors, such as tendamistat, trestatin and A1-3688, etc., (viii) insulin secretagogues, such as linogliride and A-4166, etc., (ix) fatty acid oxidation inhibitors, such as clomoxir and etomoxir, etc., (x) A2 antagonists, such as midaglizole, isaglidole, deriglidole, idazoxan, earoxan and flurparoxan, etc., (xi) insulin or insulin mimetics, such as biota, LP-100, novarapid, insulin detemir, insulin lispro, insulin glargine, insulin zinc suspension (lente and ultralente), Lys-Pro insulin, GLP-1 (73-7) (insulintropin) and GLP-1 (7-36)-NH$_2$), etc., (xii) non-thiazolidinediones, such as JT-501 and farglitazar (GW-2570/GI-262579), etc., (xiii) PPARα/γ dual agonists, such as MK-0767, CLX-0940, GW-1536, GW1929, GW-2433, KRP-297, L-796449, LR-90 and SB 219994, etc., (xiv) other insulin sensitizing drugs, and (xv) VPAC2 receptor agonists.

(b) Lipid lowering agents, such as (i) bile acid sequestrants, such as cholestyramine, colesevelem, colestipol, dialkylaminoalkyl derivatives of a corss-linked dextran, Colestid®&, LoCholest® and Questran®, etc., (ii) HMG-CoA reductase inhibitors, such as atovastatin, itavastatin, fluvastatin, lovastatin, pravastatin, rivastatin, rosuvastatin, simvastatin and ZD-4522, etc., (iii) HMG-CoA synthase inhibitors, (iv) cholesterol absorption inhibitors, such as stanol esters, beta-sitosterol, sterol glycosides such as tiqueside, and azetidinones such as ezetimibe, etc., (v) acyl coenzyme A-cholesterol acyl transferase (ACAT) inhibitors, such as avasimibe, eflucimibe, KY505, SMP 797, etc., (vi) CETP inhibitors, such as JTT 705, torcetrapib, CP 532,632, BAY63-2149, SC 591, SC 795, etc., (vii) squalene synthetase inhibitors, (viii) anti-oxidants, such as probucol, etc., (ix) PPARα agonsits, such as beclofibrate, benzafibrate, ciprofibrate, clofibrate, etofibrate, fenofibrate, gemcabene, and gemfibrozil, GW 7647, BM 170744, LY518674, and other fibric acid derivatives, such as Atromid®, Lopid®, Tricor®, etc., (x) FXR receptors, such as GW 4064, SR 103912, etc., (xi) LXR receptor modulators, such as GW 3965, T9013137 and XTC0179628, etc., (xii) lipoprotein synthesis inhibitors such as niacin, (xiii) renin angiotensin system inhibitors; (xiv) PPARδ partial agonists, (xv) bile acid reabsorption inhibitors, such as BARI 1453, SC435, PHA384640, S8921, AZD7706, etc.; (xvi) PPARδ agonists such as GW 501516 and GW 590735, etc., (xvii) triglyceride synthesis inhibitors, (xviii) microsomal triglyceride transport (MTTP) inhibitors, such as inplitapide, LAB687, and CP346086, etc., (xiv) transcription modulators, (xx) squalene epoxidase inhibitors, (xxi) low density lipoprotein (LDL) receptor inducers, (xxii) platelet aggregation inhibitors, (xxiii) 5-LO or FLAP inhibitors, and (xxiv) niacin receptor agonists; and (c) Anti-hypertensive agents, such as (i) diuretics, such as thiazides, including chlorthalidone, chlorthiazide, dichlorophenamide, hydroflumethiazide, indapamide, and hydrochlorothiazide, loop diuretics, such as bumetanide, ethacrynic acid, furosemide and torsemide, potassium sparing agents, such as amiloride, and triamterene, and aldosterone antagonists, such as spironolactone, epirenone, etc., (ii) beta-adrenergic blockers, such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, etc., (iii) calcium channel blockers, such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine and verapamil, etc., (iv) angiotensin converting enzyme (ACE) inhibitors, such as benazepril, captopril, cilazapril, delapril, enalapril, fosinopril, imidapril, losinopril, moexipril, quinapril, quinaprilat, ramipril, perindopril, perindropril, quanipril, spirapril, tenocapril, trandolapril and zofenopril, etc., (v) neutral endopeptidase inhibitors, such as omapatrilat, cadoxatril and ecadotril, fosidotril, sampatrilat, AVE7688, ER4030, etc., (vi) endothelin antagonists, such as tezosentan, A308165, and YM62899, etc., (vii) vasodilators, such as hydralazine, clonidine, minoxidil and nicotinyl alcohol, etc., (viii) angiotensin II receptor antagonists, such as candesartan, eprosartan, irbesartan, losartan, pratosartan, tasosartan, telmisartan, valsartan, and EXP-3137, F16828K, and RNH6270, etc., (ix) α/β adrenergic blockers, such as nipradilol, arotinolol and amosulalol, etc., (x) alpha 1 blockers, such as terazosin, urapidil, prazosin, bunazosin, trimazosin, doxazosin, naftopidil, indoramin, WHIP 164, and XEN010, etc., (xi) alpha 2 agonists, such as lofexidine, tiamenidine, moxonidine, rilmenidine and guanobenz, etc., and (xii) aldosterone inhibitors, etc., and (d) Anti-obesity agents, such as (i) 5HT (serotonin) transporter inhibitors, such as paroxetine, fluoxetine, fenfluramine, fluvoxamine, sertraline, and imipramine, (ii) NE (norepinephrine) transporter inhibitors, such as GW 320659, despiramine, talsupram, and nomifensine, (iii) CB-1 (cannabinoind-1 receptor) antagonist/inverse agonists, such as rimonabant (Sanofi Synthelabo), SR-147778 (Sanofi Synthelabo), BAY 65-2520 (Bayer), and SLV 319 (Solvay), and those compounds disclosed in U.S. Pat. Nos. 5,532,237, 4,973,587, 5,013,837, 5,081,122, 5,112,820, 5,292,736, 5,624,941 and 6,028,084, and WO 96/33159, WO 98/33765, WO 98/43636, WO 98/43635, WO 01/09120, WO 01/96330, WO 98/31227, WO 98/41519, WO 98/37061, WO 00/10967, WO 00/10968, WO 97/29079, WO 99/02499, WO 01/58869, WO 02/076949, WO 01/64632, WO 01/64633, WO 03/006007 and WO 03/007887, and EPO Application No. EP-658546, (iv) ghrelin antagonists, such as those disclosed in WO 01/87335, and WO 02/08250, (v) H3 (histamine H3) antagonist/inverse agonists, such as thioperamide, 3-(1H-imidazol-4-yl)propyl N-(4-pentenyl)carbamate, clobenpropit, iodophenpropit, imoproxifan, GT2394 (Gliatech), and A331440, and those compounds disclosed in WO 02/15905, and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem., 43:3335-43 (2000)), (vi) melanin-concentrating hormone 1 receptor (MCH1R) antagonists, such as T-226296 (Takeda), SNP-7941 (Synaptic), and those compounds disclosed in WO 01/82924, WO 01/87834, WO 02/051809, WO 02/06245, WO 02/076929, WO 02/076947, WO 02/04433, WO 02/51809, WO 02/083134, WO 02/094799, WO 03/004027 and Japanese Patent Application No. JP 13226269, (vii) MCH2R (melanin concentrating hormone 2R) agonist/antagonists, (viii) NPY1 (neuropeptide Y Y1) antagonists, such as BIBP3226, 2-[1-(5-chloro-3-isopropyloxycarbonylaminophenyl)ethylamino]-6-[2-(5-ethyl-4-methyl-1,3-thiazol-2-yl)ethyl]-4-morpholinopyridine, BIBO 3304, LY-357897, CP-671906, and GI-264879A, and those compounds disclosed in U.S. Pat. No. 6,001,836, and WO 96/14307, WO 01/23387, WO 99/51600, WO 01/85690, WO 01/85098, WO 01/85173 and WO 01/89528, (ix) NPY5 (neuropeptide YY5) antagonists, such as L-152,804, GW-569180A, GW-594884A, GW-587081X, GW-548118X, FR 235,208, FR-226928, FR240662, FR252384, 1229U91, GI-264879A, CGP71683A, LY-377897, LY366377, PD-160170, SR-120562A, SR-120819A, JCF-104, and H409/22, and those compounds disclosed in U.S. Pat. Nos. 6,140,354, 6,191,160, 6,258,837, 6,313,298, 6,337,332, 6,329,395 and 6,340,683, U.S. Pat. Nos. 6,326,375, 6,329,395, 6,337,332 and 6,335,345, European Patent Nos. EP-01010691 and EP-01044970, and PCT International Patent Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/23388, WO 01/23389, WO 01/44201, WO 01/62737, WO 01/62738, WO 01/09120, WO 02/20488, WO 02/22592, WO 02/48152, WO 02/49648 and WO 02/094789, and Norman et al., J. Med. Chem. 43:4288-4312 (2000), (x) leptin, such as recombinant human leptin (PEG-OB, Hoffman La Roche) and recombinant methionyl human leptin (Amgen), (xi) leptin derivatives, such as those compounds disclosed in U.S. Pat. Nos. 5,552,524, 5,552,523, 5,552,522 and 5,521,283, and PCT International Publication Nos. WO 96/23513, WO 96/23514, WO 96/23515, WO 96/23516, WO 96/23517, WO 96/23518, WO 96/23519, and WO 96/23520, (xii) opioid antagonists, such as nalmefene (Revex®), 3-methoxynaltrexone, naloxone, and naltrexone, and those compounds disclosed in WO 00/21509, (xiii) orexin antagonists, such as SB-334867-A, and those compounds disclosed in WO 01/96302, WO 01/68609, WO 02/51232, WO 02/51838 and WO 03/023561, (xiv) BRS3 (bombesin receptor subtype 3) agonists, (xv) CCK-A (cholecystokinin-A) antagonists, such as AR-R 15849, GI 181771, JMV-180, A-71378, A-71623 and SR146131, and those disclosed in U.S. Pat. No. 5,739,106, (xvi) CNTF (ciliary neurotrophic factors), such as GI-181771 (Glaxo-SmithKline), SR146131 (Sanofi Synthelabo), butabindide, and PD170,292 and PD149164 (Pfizer), (xvii) CNTF derivatives, such as axokine (Regeneron) and those compounds disclosed in WO 94/09134, WO 98/22128 and WO 99/43813, (xviii) GHS (growth hormone secretagogue receptor) agonists, such as NN703, hexarelin, MK-0677, SM-130686, CP-424,391, L-692,429 and L-163,255, and those compounds disclosed in U.S. Pat. No. 6,358,951, U.S. Patent Application Nos. 2002/049196 and 2002/022637, and WO 01/56592 and WO 02/32888, (xix) 5HT2c (serotonin receptor 2c) agonists, such as BVT933, DPCA37215, IK264, PNU 22394, WAY161503, R-1065 and YM 348, and those compounds disclosed in U.S. Pat. No. 3,914,250, and WO 02/36596, WO 02/48124, WO 02/10169, WO 01/66548, WO 02/44152, WO 02/51844, WO 02/40456 and WO 02/40457, (xx) Mc3r (melanocortin 3 receptor) agonists, (xxi) Mc4r (melanocortin 4 receptor) agonists, such as CHIR86036 (Chiron), ME-10142 and ME-10145 (Melacure), and those compounds disclosed in WO 99/64002, WO 00/74679, WO 01/991752, WO 01/74844, WO 01/70708, WO 01/70337, WO 01/91752, WO 02/059095, WO 02/059107, WO 02/059108, WO 02/059117, WO 02/12166, WO 02/11715, WO 02/12178, WO 02/15909, WO 02/068387, WO 02/068388, WO 02/067869, WO 03/007949 and WO 03/009847, (xxii) monoamine reuptake inhibitors, such as sibutratmine (Meridia®/Reductil®) and salts thereof, and those compounds disclosed in U.S. Pat. Nos. 4,746,680, 4,806,570 and 5,436,272, and U.S. Patent Publication No. 2002/0006964, and WO 01/27068 and WO 01/62341, (xxiii) serotonin reuptake inhibitors, such as dexfenfluramine, fluoxetine and those compounds disclosed in U.S. Pat. No. 6,365,633, and WO 01/27060 and WO 01/162341, (xxiv) GLP-1 (glucagon-like peptide 1) agonists, (xxv) Topiramate (Topimax®), (xxvi) phytopharm compound 57 (CP 644,673), (xxvii) ACC2 (acetyl-CoA carboxylase-2) inhibitors, (xxviii) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114 and SR 59119A, and those compounds disclosed in U.S. Pat. No. 5,705,515, U.S. Pat. No. 5,451,677, and WO 01/74782, WO 02/32897, (xxix) DGAT1 (diacylglycerol acyltransferase 1) inhibitors, (xxx) DGAT2 (diacylglycerol acyltransferase 2) inhibitors, (xxxi) FAS (fatty acid synthase) inhibitors, such as Cerulenin and C75, (xxxii) PDE (phosphodiesterase) inhibitors, such as theophylline, pentoxifylline, zaprinast, sildenafil, aminone, milrinone, cilostanide, rolipram and cilomilast, (xxxiii) thyroid hormone β agonists, such as KB-2611 (KaroBioBMS), and those compounds disclosed in WO 02/15845 and Japanese Patent Application No. JP 2000256190, (xxxiv) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid, and those compounds disclosed in WO 99/00123, (xxxv) acyl-estrogens, such as oleoyl-estrone disclosed in del Mar-Grasa, M. et al., Obesity Research, 9:202-9 (2001), (xxxvi) glucocorticoid antagonists, (xxxvii) 11β HSD-1 (11-beta hydroxy steroid dehydrogenase type 1) inhibitors, such as BVT 3498, BVT 2733, and those compounds disclosed in WO 01/90091, WO 01/90090, WO 01/90092, (xxxviii) SCD-1 (stearoyl-CoA desaturase-1) inhibitors, (xxxix) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, and those compounds disclosed in WO 03/004498, WO 03/004496, EP 1258476, WO 02/083128, WO 02/062764, WO 03/000250, WO 03/002530, WO 03/002531, WO 03/002553, WO 03/002593, WO 03/000180 and WO 03/000181, (xxxx) lipase inhibitors, such as tetrahydrolipstatin (orlistat/Xenical®), Triton WR1339, RHC80267, lipstatin, teasaponin and diethylumbelliferyl phosphate, FL-386, WAY-121898, Bay-N-3176, valilactone, esteracin, ebelactone A, ebelactone B, and RHC 80267, and those compounds disclosed in WO 01/77094, and U.S. Pat. Nos. 4,598,089, 4,452,813, 5,512,565, 5,391,571, 5,602,151, 4,405,644, 4,189,438, and 4,242,453, (xxxxi) fatty acid transporter inhibitors, (xxxxii) dicarboxylate transporter inhibitors, (xxxxiii) glucose transporter inhibitors, (xxxxiv) phosphate transporter inhibitors, (xxxxv) melanocortin agonists, such as Melanotan II or those compounds described in WO 99/64002 and WO 00/746799, (xxxxvi) melanin concentrating hormone antagonists, (xxxxvii) galanin antagonists, (xxxxviii) CCK agonists, (xxxxix) corticotropin-releasing hormone agonists, and (xxxxx) phosphodiesterase-3B (PDE3B) inhibitors and the like.

The above combinations include combinations of the composition of the present invention not only with one of other active compounds, but also with two or more of other active compounds. Non-limiting examples include combinations of the compositions of the present invention with one, two or more active compounds selected from lipid-lowering agents, and anti-hypertensive agents. Combinations of the compositions of the present invention with one, two or more active compounds selected from lipid lowering agents, and anti-diabetic agents are useful to treat, control or prevent metabolic syndrome. In particular, compositions comprising an anti-obesity agent and an anti-hypertensive agent, in addition to an anti-diabetic agent and/or a lipid lowering agent, will be useful to synergistically treat, control or prevent metabolic syndrome.

BEST MODE FOR CARRYING OUT THE INVENTION

The Examples are described below to illustrate the present invention more particularly, but the present invention shall not be limited thereto.

The mass spectrum was determined by electron spray ionization (ESI) method by use of Quattro II.

In the Examples, THF and DMF stand for tetrahydrofuran and dimethylformamide, respectively.

Example 1

Preparation of 2-(trans-4-tert-butylsulfonylamino-cyclohexyl)-5-(trifluoromethyl)benzimidazole 1) Preparation of ethyl 4-tert-butylsulfinylaminocyclohexanecarboxylate 2-Methyl-2-propanesulfinamide (854 mg) and titanium (IV) ethoxide (3.0 mL) were added to a toluene solution (5 mL) containing ethyl 4-ketocyclohexanecarboxylate (1.0 g) at room temperature, followed by stirring under heating for 1 hr at 70° C. The reaction mixture was cooled to room temperature and admixed with sodium borohydride (854 mg) and then methanol (5.0 mL), followed by stirring for 30 min. The reaction mixture was admixed with an aqueous saturated sodium-chloride solution, and after the resultant insoluble matter was filtered out, the organic layer was concentrated under reduced pressure. The residue was separated and purified by silica-gel column chromatography (C-300, hexane: ethyl acetate=1:2) to give the title compound (1.42 g) composed mainly of the trans isomer.

2) Preparation of 4-tert-butylsulfonylaminocyclohexanecarboxylic acid

Metachloroperbenzoic acid (1.25 g) was added, under cooling with ice, to a methylene chloride solution (10 mL) containing ethyl 4-tert-butylsulfinylaminocyclohexane-carboxylate (1.0 g) as prepared by the above-described preparation method, and stirring was effected at room temperature for 3 hrs. The reaction mixture, after being diluted with ethyl acetate, was washed with an aqueous saturated sodium-hydrogencarbonate and sodium-chloride solutions successively, dried over anhydrous sodium sulfate and concentrated under reduced pressure. The resultant residue was separated and purified by silica-gel chromatography (C-300, hexane: ethyl acetate=1:1) to give ethyl 4-tert-butylsulfonylamino-cyclohexanecarboxylate composed mainly of the trans isomer (673 mg).

The compound (455 mg) was dissolved in methanol (10 mL), and the solution was admixed with a 1N aqueous sodium hydroxide solution (3.5 mL), followed by stirring at room temperature for 16 hrs. The reaction solution was ice-cooled, neutralized with 1N hydrochloric acid (3.5 mL) and concentrated under reduced pressure, and the residue was extracted with ethyl acetate. The organic layer was washed with an aqueous saturated sodium chloride solution, dried over anhydrous sodium sulfate and then concentrated under reduced pressure to give the title compound composed mainly of the trans isomer (413 mg).

3) Preparation of 2-(trans-4-tert-butylsulfonylami-nocyclohexyl)-5-(trifluoromethyl)benzimidazole Hydrochloride of 1-(3-dimethylaminopropyl)-3-ethylcarbodiimide (87 mg) and 1-hydroxybenzotriazole (90 mg) were added to a DMF solution (4.0 mL) containing 4-tert-butylsulfonylaminocyclohexanecarboxylic acid (99 mg) as prepared by the above-described preparation method and 4-trifluoromethyl-1,2-phenylenediamine (66 mg), followed by stirring at room temperature for 16 hrs. The reaction solution was diluted with ethyl acetate, and the organic layer was washed with aqueous saturated sodium hydrogencarbonate and sodium chloride solutions, successively, dried over anhydrous sodium sulfate and then concentrated under reduced pressure to give a crude amide containing trans-N-(2-amino-5-trifluoromethylphenyl)-4-tertbutylsulfonylaminocyclo-hexanecarboxamide. The crude amide was admixed with phosphorus oxychloride (1.0 mL), and the mixture was heated under stirring at 100° C. for 2 hrs. The excess phosphorus oxychloride was distilled off under reduced pressure, and the residue was diluted with ethyl acetate. The organic layer was washed with aqueous saturated sodium hydrogencarbonate and sodium chloride solutions successively, dried over anhydrous sodium sulfate and concentrated under reduced pressure, and the residue was crystallized from isopropyl ether to give the title compound (48.2 mg).

$^1$HNMR (400 MHz, CDCl$_3$, δppm): 1.68-1.92 (2H, m), 2.18-2.40 (6H, m), 3.20-3.48 (1H, m), 3.90-4.10 (1H, m), 7.48 (1H, d, J=7.6 Hz), 7.61 (1H, d, J=7.6 Hz), 7.82 (1H, s); Mass spectrum (ESI): 404 (M+H)

Example 2

Preparation of 2-(trans-4-tert-butylsulfonylamino-cyclohexyl)-5-(2-methyltetrazol-5-yl)benzimidazole By following the same procedure as described in Example 1 except that 4-(2-methyltetrazol-5-yl)-1,2-phenylenediamine was used in place of 4-trifluoromethyl-1,2-phenylenediamine, the title compound was prepared.

$^1$HNMR (400 MHz, CDCl$_3$, δppm): 1.62-1.90 (2H, m), 2.10-2.56 (2H, m), 2.80-2.98 (1H, m), 2.80-2.98 (1H, m), 3.20-3.40 (2H, m), 3.62-3.80 (1H, m), 4.38 (3H, s), 7.65 (1H, d, J=8.0 Hz), 7.98 (1H, d, J=8.0 Hz), 8.27 (1H, s); Mass spectrum (ESI): 418 (M+H)

Example 3

Preparation of 2-(trans-4-tert-butylsulfonylamino-cyclohexyl)-5-phenylbenzimidazole By following the same procedure as described in Example 1 except that 4-phenyl-1,2-phenylenediamine was used in place of 4-trifluoromethyl-1,2-phenylenediamine, the title compound was prepared.

$^1$HNMR (400 MHz, CD$_3$OD, δppm): 1.38 (9H, s), 1.40 1.62 (2H, m), 1.70-1.84 (2H, m), 2.10-2.30 (4H, m), 2.80-2.98 (1H, m), 4.42-4.98 (1H, m), 7.22-7.38 (1H, m), 7.38-7.70 (6H, m), 7.69 (1H, s); Mass spectrum (ESI): 412 (M+H)

Example 4

Preparation of 2-(trans-4-tert-butylsulfonylamino-cyclohexyl)-5-(2-fluorophenyl)imidazo[4,5-b]pyridine By following the same procedure as described in Example 1 except that 2,3-diamino-6-(2-fluorophenyl)pyridine was used in place of 4-trifluoromethyl-1,2-phenylenediamine, the title compound was prepared.

$^1$HNMR (400 MHz, CDCl$_3$, δppm): 1.10 1.80 (4H, m), 1.41 (9H, s), 2.00-2.30 (4H, m), 2.50-2.70 (1H, m), 3.20-3.40

(1H, m), 3.69 (1H, s, J=8.8 Hz), 7.12-7.44 (3H, m), 7.69 (1H, d, J=8.4 Hz), 7.82-8.00 (1H, m), 8.05 (1H, d, J=8.4 Hz); Mass spectrum (ESI): 431 (M+H)

Example 5

Preparation of 8-(trans-4-tert-butylsulfonylamino-cyclohexyl)-2-(2-fluorophenyl)purine By following the same procedure as described in Example 1 except that 4,5-diamino-2-(2-fluorophenyl)pyrimidine was used in place of 4-trifluoromethyl-1,2-phenylenediamine, the title compound was prepared.

$^1$HNMR (400 MHz, CDCl$_3$, δppm): 0.82 1.60 (13H, m), 1.92-2.40 (4H, m), 3.20-3.44 (2H, m), 7.16-7.40 (2H, m), 7.42-7.60 (1H, m), 8.16 (1H, t, J=6.0 Hz); Mass spectrum (ESI): 432 (M+H)

Example 6

Preparation of 8-(cis-4-tert-butylsulfonylamino-cyclohexyl)-2-(2-fluorophenyl)purine By following the same procedure as described in Example 1 except that use was made of 4,5-diamino-2-(2-florophenyl)-pyrimidine and cis-4-tert-butylsulfonylaminocyclohexane-carboxylic acid as prepared from cis-4-aminocyclohexane-carboxylic acid in accordance with the 1$^{st}$, 2$^{nd}$ and 4$^{th}$ steps of Example 4 described in WO0137826 in place of 4-trifluoromethyl-1,2-phenylenediamine, the title compound was prepared.

$^1$HNMR (400 MHz, CDCl$_3$, δppm): 1.12 2.14 (8H, m), 1.44 (9H, s), 2.82-3.02 (1H, m), 3.62-3.78 (1H, m), 5.22-5.42 (1H, m), 7.02-7.30 (2H, m), 7.30-7.50 (2H, m), 7.98-8.10 (1H, m), 9.11 (1H, s); Mass spectrum (ESI): 432 (M+H)

Example 7

Preparation of 8-(trans-4-tert-butylsulfonylamino-cyclohexyl)-2-(4-fluorophenyl)purine By following the same procedure as described in Example 1 except that 4,5-diamino-2-(4-fluorophenyl)pyrimidine was used in place of 4-trifluoromethyl-1,2-phenylenediamine, the title compound was prepared.

$^1$HNMR (300 MHz, DMSO-d$_6$, δppm): 1.27 (9H, s), 1.34 1.54 (2H, m), 1.54-1.75 (2H, m), 1.82-2.28 (4H, m), 2.70-2.90 (1H, m), 3.04-3.40 (1H, m), 6.88 (1H, d, J=8.7 Hz), 7.25-7.35 (2H, m), 8.35-8.49 (2H, m), 9.02 (1H, s); Mass spectrum (ESI): 432 (M+H)

Example 8

Preparation of 8-(cis-4-tert-butylsulfonylamino-cyclohexyl)-2-(4-fluorophenyl)purine By following the same procedure as described in Example 1 except that use was made of 4,5-diamino-2-(4-fluorophenyl)pyrimidine and cis-4-tert-butylsulfonylaminocyclohexanecarboxylic acid in place of 4-trifluoromethyl-1,2-phenylenediamine, the title compound was prepared.

$^1$HNMR (300 MHz, CDCl$_3$, δppm): 1.62 2.22 (8H, m), 1.51 (9H, s), 3.00-3.20 (1H, m), 3.76-3.98 (1H, m), 5.88-6.08 (1H, m), 7.04-7.20 (2H, m), 8.34-8.64 (2H, m), 8.88-9.10 (1H, m); Mass spectrum (ESI): 432 (M+H)

Example 9

Preparation of 8-(trans-4-tert-butylsulfonylamino-cyclohexyl)-2-phenylpurine

By following the same procedure as described in Example 1 except that 4,5-diamino-2-phenylpyrimidine was used in place of 4-trifluoro-methyl-1,2-phenylenediamine, the title compound was prepared.

$^1$HNMR (400 MHz, CDCl$_3$, δppm): 1.14 1.82 (4H, m), 2.00-2.40 (4H, m), 2.60-2.80 (1H, m), 3.20-3.40 (1H, m), 7.38-7.60 (3H, m), 8.30-8.48 (2H, m), 9.11 (1H, s), 10.6 (1H, brs); Mass spectrum (ESI): 414 (M+H)

Example 10

Preparation of 8-(cis-4-tert-butylsulfonylamino-cyclohexyl)-2-phenylpurine

By following the same procedure as described in Example 1 except that use was made of 4,5-diamino-2-phenylpyrimidine and cis-4-tert-butylsulfonylaminocyclohexanecarboxylic acid in place of 4-trifluoromethyl-1,2-phenylenediamine, the title compound was prepared.

$^1$HNMR (400 MHz, CDCl$_3$, δppm): 1.20 2.20 (8H, m), 2.96-3.14 (1H, m), 3.62-3.90 (1H, m), 7.38-7.60 (3H, m), 8.38-8.60 (2H, m), 9.07 (1H, s), 10.3 (1H, brs); Mass spectrum (ESI): 414 (M+H)

Example 11

Preparation of 5-(2,4-difluorophenyl)-2-(trans-4-isopropylsulfonylaminocyclohexyl)imidazo[4,5-b]pyridine and its cis isomer 4-isopropylsulfonylaminocyclohexanecarboxylic acid as prepared easily from methyl 4-aminocyclohexanecarboxylate with 2-propanesulfonyl chloride, and 2,3-diamino-6-(2,4-difluorophenyl)pyridine were allowed to undergo ring-closure condensation under the same conditions as described in Example 1-3), followed by separatory purification on a collective thin-layer chromatograph (chloroform:methanol=20:1) to give the title compounds.

Trans Isomer (More Polar Substance):

$^1$HNMR (400 MHz, CDCl$_3$, δppm): 0.82 2.22 (14H, m), 2.82-3.30 (2H, m), 3.60-3.80 (1H, m), 4.80-5.20 (1H, m), 6.82-7.10 (2H, m), 7.60-7.70 (1H, m), 7.80-8.10 (2H, m); Mass spectrum (ESI): 435 (M+H)

Cis Isomer (Less Polar Substance):

$^1$HNMR (400 MHz, CDCl$_3$, δppm): 1.60 2.38 (14H, m), 3.00-3.18 (1H, m), 3.38-3.56 (1H, m), 3.72-3.84 (1H, m), 6.08-6.36 (1H, m), 6.84-7.08 (2H, m), 7.91 ((1H, dd, J=8.8 Hz, 14.8 Hz), 8.21 (1H, d, J=8.8 Hz); Mass spectrum (ESI): 435 (M+H)

Example 12

Preparation of 2-(trans-4-methylsulfonylaminocyclohexyl)-5-phenylbenzimidazole

To a solution in a solvent mixture of THF (4.0 mL) and water (1.0 mL) of 2-(trans-4-azidocyclohexyl)-5-phenylbenzimidazole (73.1 mg) as prepared by reacting trans-4-azidocyclohexanecarboxylic acid with 4-phenyl-1,2-phenylenediamine under the same conditions as described in Example 1-3) was added triphenylphosphine (72.0 mg), followed by stirring at room temperature for 1 hr. A portion of the reaction solution was admixed with methanesulfonyl chloride and triethylamine, followed by stirring at the same temperature for 1 hr., and the resultant reaction solution was admixed with conc. aqueous ammonia, followed by concentration under reduced pressure. The residue was separated and purified on a collective thin-layer chromatograph (chloroform:methanol=15:1) to give the title compound.

$^1$HNMR (400 MHz, CDCl$_3$, δppm): 1.70 2.22 (8H, m), 2.98-3.20 (1H, m), 3.08 (3H, s), 3.62-3.90 (1H, m), 5.60-5.80 (1H, m), 7.18-7.82 (8H, m); Mass spectrum (ESI): 370 (M+H)

Example 13

Preparation of 5-phenyl-2-(trans-4-p-tolylsulfonylamino-cyclohexyl)benzimidazole By carrying out the same reaction as described in Example 12 except that p-toluenesulfonyl chloride was used in place of methansulfonyl chloride, the title compound was prepared.

$^1$HNMR (400 MHz, CDCl$_3$, δppm): 1.22 1.48 (2H, m), 1.48-1.70 (2H, m), 1.70-1.85 (2H, m), 1.95-2.10 (2H, m), 2.40 (3H, s), 2.75-3.10 (2H, m), 7.30-7.80 (12H, m); Mass spectrum (ESI): 446 (M+H)

Example 14

Preparation of 2-(cis-4-methylsulfonylaminocyclohexyl)-5-phenylbenzimidazole

By carrying out the same reaction as described in Example 12 except that cis-4-azidocyclohexanecarboxylic acid was used in place of trans-4-azidocyclohexanecarboxylic acid, the title compound was prepared.

$^1$HNMR (400 MHz, CDCl$_3$, δppm): 1.60 2.56 (8H, m), 2.70-3.00 (1H, m), 2.92 (3H, s), 3.20-3.40 (1H, m), 7.18-7.80 (8H, m); Mass spectrum (ESI): 370 (M+H)

Example 15

Preparation of 5-phenyl-2-(cis-4-p-tolylsulfonylaminocyclohexyl)benzimidazole

By carrying out the same reaction as described in Example 14 except that p-toluenesulfonyl chloride was used in place of methansulfonyl chloride, the title compound was prepared.

$^1$HNMR (300 MHz, CDCl$_3$, δppm): 1.50 1.69 (4H, m), 1.80-2.00 (2H, m), 2.00-2.20 (2H, m), 2.40 (3H, s), 3.15-3.50 (2H, m), 7.37-7.59 (5H, m), 7.68-7.98 (7H, m); Mass spectrum (ESI): 446 (M+H)

Example 16

Preparation of 2-{trans-4-(N-methyl-tert-butylsulfonylamino)cyclohexyl}-5-phenylbenzimidazole 1) Preparation of trans-4-(N-methyl-tert-butylsulfonylamino)cyclohexanecarboxylic acid To a DMF solution (3.0 mL) containing ethyl trans-4-tert-butylsulfonuylaminocyclohexanecarboxylate (82 mg) were added 60% sodium hydride (14 mg) and methyl iodide (0.025 mL), followed by stirring at 0° C. for 30 min. The reaction mixture was admixed with an aqueous ammonium chloride solution, followed by extraction with ethyl acetate. The organic layer was washed with water and an aqueous saturated sodium chloride solution successively, dried over anhydrous sodium sulfate and concentrated under reduced pressure. The residue was dissolved in ethanol (0.5 mL), and the solution was admixed with 1N aqueous sodium hydroxide solution (0.5 mL), followed by stirring at room temperature for 2 hrs. The reaction mixture was neutralized with 1N hydrochloric acid and extracted with chloroform, and the chloroform layer was dried over anhydrous sodium sulfate and concentrated under reduced pressure to give the title compound.

2) Preparation of 2-{trans-4-(N-methyl-tert-butylsulfonylamino)cyclohexyl}-5-phenylbenzimidazole Trans-4-(N-methyl-tert-butylsulfonylamino)cyclohexanecarboxylic acid and 4-phenyl-1,2-phenylenediamine were allowed to undergo ring closure condensation under the same conditions as described in Example 1-3), followed by separatory purification on a collective thin-layer chromatograph (chloroform:methanol=10:1) to give the title compound.

$^1$HNMR (400 MHz, CDCl$_3$, δppm): 1.39 (9H, s), 1.70-1.98 (4H, m), 1.98-2.16 (2H, m), 2.22-2.42 (2H, m), 2.80-3.00 (1H, m), 2.89 (3H, s), 3.64-3.86 (1H, m), 7.20-7.80 (6H, m), 7.63 (2H, d, J=7.6 Hz); Mass spectrum (ESI): 426 (M+H)

Example 17

Preparation of 2-(4-tert-butylsulfonylaminopiperidin-1-yl)-5-phenylbenzimidazole 1) Preparation of 4-tert-butylsulfinylamino-1-ethoxycarbonylpiperidine By carrying out the same reaction as described in Example 1-1) except that 1-ethoxycarbonylpiperidin-4-on was used in place of ethyl 4-ketocyclohexanecarboxylate, the title compound was prepared.

Preparation of 1-cyano-4-(tert-butylsulfinylamino)-piperidine

To a 2-propanol solution (35 mL) containing 4-tert-butylsulfinylamino-1-ethoxycarbonylpiperidine (2.5 g) were added, at room temperature, water (35 mL) and barium hydroxide hydrate (11.7 g), followed by heating under reflux for 4 hrs. The reaction mixture was cooled to room temperature, and the resultant insolubles were filtered out, whereafter the mother liquor was concentrated under reduced pressure. The residue was dissolved in DMF (10 mL), and cyanogen bromide (400 mg) and triethylamine (1.2 mL) were added to the solution at room temperature, followed by stirring for 16 hrs. The reaction mixture was diluted with ethyl acetate and water, and the water layer was furthermore extracted with chloroform. The chloroform layer was washed with an aqueous saturated sodium chloride solution, dried over anhydrous sodium sulfate and concentrated under reduced pressure. The residue was separated and purified on a silica-gel column chromatograph (C-300, chloroform:methanol=50:1) to give the title compound (250 mg).

2) Preparation of 1-cyano-4-(tert-butylsulfonylamino)piperidine

Meta-chloroperbenzoic acid (60 mg) was added to the chloroform solution (0.5 mL) containing 1-cyano-4-(tert-butylsulfinyl-amino)piperidine at room temperature, followed by stirring at the same temperature for 16 hrs. The reaction mixture was diluted with ethyl acetate, and the organic layer was washed with aqueous saturated sodium hydrogencarbonate and aqueous saturated sodium chloride solutions successively, dried over anhydrous sodium sulfate and concentrated under reduced pressure to give the title compound (58 mg).

3) Preparation of 2-(4-tert-butylsulfonylaminopiperidin-1-yl)-5-phenylbenzimidazole To the toluene solution (1 mL) containing 1-cyano-4-(tert-butylsulfonylamino)piperidine (22 mg) were added 4-phenyl-1,2-phenylenediamine (20 mg) and ytterbium triflate (20 mg), and the mixture was stirred in a sealed tube at 130° C. for 16 hrs. The reaction mixture was cooled to room temperature and diluted with ethyl acetate. The organic layer was washed with aqueous saturated sodium hydrogencarbonate solution and aqueous saturated sodium chloride solutions successively, dried over anhydrous sodium sulfate and concentrated under reduced pressure. The residue was separated and purified on a collective thin-layer chromatograph (chloroform: methanol=15:1) to give the title compound (12 mg).
$^1$HNMR (400 MHz, CDCl$_3$, δppm): 1.40 (9H, m), 1.50-1.70 (2H, m), 2.00-2.18 (2H, m), 3.00-3.20 (2H, m), 3.38-3.58 (1H, m), 3.96-4.16 (2H, m), 4.40-4.58 (1H, m), 7.18-7.42 (3H, m), 7.42-7.62 (2H, m); Mass spectrum (ESI): 413 (M+H)

Example 18

Preparation of 2-(4-tert-butylsulfonylaminopiperidin-1-yl)-5-(2-methyltetrazol-5-yl)benzimidazole By carrying out the same reaction as described in Example 17 except that 4-(2-methyltetrazol-5-yl)-1,2-phenylene-diamine was used in place of 4-phenyl-1,2-phenylenediamine, the title compound was prepared.
$^1$HNMR (400 MHz, CDCl$_3$, δppm): 1.52-1.74 (2H, m), 2.08-2.22 (2H, m), 3.08-3.20 (2H, m), 3.40-3.60 (1H, m), 4.04-4.20 (2H, m), 4.20-4.40 (1H, m), 4.35 (3H, s), 7.39 (1H, d, J=8.0 Hz), 7.84 (1H, d, J=8.0 Hz), 8.00 (1H, s); Mass spectrum (ESI): 419 (M+H)

Example 19

Preparation of 2-(3-isopropylsulfonyl-cis-3,7-diazabicyclo-[3.3.0]octan-7-yl)-5-phenylbenzimidazole 1) Preparation of 2-(3-tert-butoxycarbonyl-cis-3,7-diazabicyclo[3.3.0]oct-7-yl)-5-phenylbenzimidazole 2-Chloro-5-phenylbenzimidazole (34 mg) was added to the N-methylpyrrolidone solution (0.2 mL) containing 3-tert-butoxycarbonyl-cis-3,7-diazabicyclo[3.3.0]octane (62 mg), followed by stirring at 150° C. for 4 hrs. The reaction mixture was cooled to room temperature and concentrated under reduced pressure. The residue was separated and purified on a silica-gel column chromatograph (C-300, chloroform: THF=4:1) to give the title compound (29 mg).

2) Preparation of 2-(cis-3,7-diazabicyclo[3.3.0]oct-3-yl)-5-phenylbenzimidazole hydrochloride 4N Hydrochloric acid/dioxane solution (1 mL) was added to 2-(3-tert-butoxycarbonyl-cis-3,7-diazabicyclo[3.3.0]oct-7-yl)-5-phenylbenzimidazole (26 mg), followed by stirring at room temperature for 1 hr. The reaction mixture was concentrated under reduced pressure to give the title compound (26 mg).

3) Preparation of 2-(3-isopropylsulfonyl-cis-3,7-diazabicyclo[3.3.0]oct-7-yl)-5-phenylbenzimidazole 2-Propanesulfonyl chloride and triethylamine were added to the THF suspension (5 mL) containing 2-(cis-3,7-diazabicyclo[3.3.0]oct-3-yl)-5-phenylbenzimidazole hydrochloride (26 mg) at room temperature, followed by stirring for 15 min. The reaction mixture was concentrated under reduced pressure, and the residue was separated and purified on a collective thin-layer chromatograph (chloroform:methanol=10:1) to give the title compound (12 mg).
$^1$HNMR (300 MHz, CDCl$_3$, δppm): 1.35 (6H, d, J=6.7 Hz), 3.02-3.28 (3H, m), 3.28-3.45 (2H, m), 3.45-3.60 (2H, m), 3.60-3.88 (4H, m), 7.20-7.65 (8H, m); Mass spectrum (ESI): 439 (M+H)

Example 20

Preparation of 2-(4-isopropylsulfonyl-cis-4,9-diazabicyclo-[5.3.0]dec-9-yl)-5-phenylbenzimidazole By following the same procedure as described in Example 19 except that 4-tert-butoxycarbonyl-cis-4,9-diazabicyclo [5.3.0]decane was used in place of 3-tert-butoxycarbonyl-cis-3,7-diazabicyclo[3.3.0]octane, the title compound was prepared.
$^1$HNMR (400 MHz, CDCl$_3$, δppm): 1.80-2.02 (4H, m), 2.60-2.78 (2H, m), 3.10-3.30 (3H, m), 3.30-3.40 (2H, m), 3.60-3.78 (2H, m), 3.78-3.90 (2H, m), 7.20-7.44 (5H, m), 7.44-7.60 (3H, m); Mass spectrum (ESI): 439 (M+H)

Example 21

Preparation of 2-(1-isopropylsulfonylpiperazin-4-yl)-5-phenylbenzimidazole

By following the same procedure as described in Example 19 except that 1-tert-butoxycarbonylpiperazine was used in place of 3-tert-butoxycarbonyl-cis-3,7-diazabicyclo[3.3.0] octane, the title compound was prepared.
$^1$HNMR (400 MHz, CD$_3$OD, δppm): 1.34 (6H, d, J=6.8 Hz), 3.33-3.40 (1H, m), 3.49-3.53 (4H, m), 3.61-3.65 (4H, m), 7.27 (1H, t, J=7.2 Hz), 7.49 (1H, s), 7.59 (2H, dd, J=1.2, 8.4 Hz); Mass spectrum (ESI): 385 (M+H)

Example 22

Preparation of 8-{1-(2-methylsulfonylaminophenyl) piperazin-4-yl}-2-phenylpurine By following the same reaction as described in Example 19 except that 1-(2-methylsulfonylaminophenyl)piperazine was used in place of 3-tert-butoxycarbonyl-cis-3,7-diazabicyclo [3.3.0]octane, and 8-chloro-2-phenylpurine was used in place of 2-chloro-5-phenylbenzimidazole, the title compound was prepared.
$^1$HNMR (400 MHz, CD$_3$OD, δppm): 3.06-3.12 (4H, m), 3.16 (3H, s), 3.90-3.97 (4H, m), 7.15-7.25 (3H, m), 7.32-7.37 (1H, m), 7.45-7.55 (3H, m), 8.32-8.35 (2H, m), 8.46 (1H, s); Mass spectrum (ESI): 450 (M+H)

Example 23

Preparation of 5-phenyl-2-{4-(N-phenylmethylsulfonylamino)piperidin-1-yl}benzimidazole By following the same procedure as described in Example 19 except that 4-(N-phenylmethylsulfonylamino)piperidine was used in place of 3-tert-butoxycarbonyl-cis-3,7-diazabicyclo[3.3.0]octane, the title compound was prepared.

$^1$HNMR (400 MHz, CD$_3$OD, δppm): 1.57 (2H, dq, J=3.9 Hz, 11.9 Hz), 1.95-2.05 (2H, m), 2.97 (3H, s), 3.05-3.20 (2H, m), 4.10-4.20 (2H, m), 4.25-4.40 (1H, m), 7.30-7.50 (10H, m), 7.47 (1H, s), 7.50-7.60 (2H, m); Mass spectrum (ESI): 447 (M+H)

Example 24

Preparation of 2-[4-(1,1-dioxo-1λ$^6$-isothiazolidin-2-yl)piperidin-1-yl]-5-phenylbenzimidazole 1) Preparation of 4-(3-chloropropylsulfonylamino)-1-benzylpiperidine 3-Chloropropanesulfonyl chloride (0.26 mL) was added to the ether solution (10 mL) containing 4-amino-1-benzylpiperidine (400 mg) at 0° C., followed by stirring for 3 hrs. The reaction mixture was concentrated under reduced pressure to give the title compound (678 mg).

2) Preparation of 4-(1,1-dioxo-1λ$^6$-isothiazolidin-2-yl)benzylpiperidine

60% Sodium hydride (106 mg) was added to the THF solution (5 mL) containing 4-(3-chloropropylsulfonylamino)-1-benzylpiperidine (330 mg) at room temperature, followed by heating under reflux for 10 hrs. The reaction mixture was cooled to room temperature and admixed with water, followed by extraction with ethyl acetate. The organic layer was washed with an aqueous saturated sodium chloride solution, dried over anhydrous sodium sulfate and concentrated under reduced pressure to give the title compound (252 mg).

3) Preparation of 4-(1,1-dioxo-1λ$^6$-isothiazolidin-2-yl)piperidine

20% Palladium hydroxide (100 mg) was added to the methanol solution (5 mL) containing 4-(1,1-dioxo-1λ$^6$-isothiazolidin-2-yl)-1-benzylpiperidine (252 mg) at 0° C., followed by stirring at room temperature for 5 hrs. under a hydrogen atmosphere. The reaction mixture was filtered to remove the palladium catalyst, followed by concentration under reduced pressure to give the title compound.

4) Preparation of 2-{4-(1,1-dioxo-1λ$^6$-isothiazolidin-2-yl)piperidin-1-yl}-5-phenyl-1-(4-methoxyphenylsulfonyl)benzimidazole To the acetonitrile solution (3 mL) containing 4-(1,1-dioxo-1λ$^6$-isothiazolidin-2-yl)piperidine (136 mg) were added 1-(4-methoxyphenylsulfonyl)-2-chloro-5-phenylbenzimidazole (340 mg) and diisopropylethylamine (0.41 mL), followed by stirring at room temperature for 16 hrs. The reaction mixture was diluted with ethyl acetate and water, and the organic layer was washed with an aqueous saturated sodium chloride solution, dried over anhydrous sodium sulfate and concentrated under reduced pressure. The residue was separated and purified on a collective thin-layer chromatograph (ethyl acetate) to give the title compound (157 mg).

5) Preparation of 2-{4-(1,1-dioxo-1λ$^6$-isothiazolidin-2-yl)piperidin-1-yl}-5-phenylbenzimidazole 2-{4-(1,1-Dioxo-1λ$^6$-isothiazolidin-2-yl)piperidin-1-yl}-5-phenyl-1-(4-methoxyphenylsulfonyl)benzimidazole (76 mg) was dissolved in 4N hydrochloric acid/dioxane solution and it is also published to be involved in anxiety and pain (Nature, vol. 259, pp. 528 (1993)); Brain Research, vol. 859, pp. 361 (2000)), while it is described that it exhibits a pressor action via its potent vasoconstrictive activity in the periphery (FEBS Letters, vol. 362, pp. 192 (1995); Nature Medicine, vol. 4, pp. 722 (1998)).

Referring to the actions that NPY can exhibit through mediation of the NPY Y2 receptor, it is known to exhibit an inhibitory action on the release of a variety of neurotransmitters at the nerve endings (British Journal of Pharmacology, vol. 102, pp. 41 (1991); Synapse, vol. 2, pp. 299 (1988)); it is observed to control the release of neurotransmitters in the periphery or to be implicated in the constriction of blood vessels or vas deferens as its direct actions (The Journal of Pharmacology and Experimental Therapeutics, vol. 261, pp. 863 (1992); British Journal of Pharmacology, vol. 100, pp. 190 (1990)); it is reported to suppress lipolysis in the adipose tissues (Endocrinology, vol. 131, pp. 1970 (1992)); and it is known to inhibit the ion secretions in the gastro-intestinal tract (British Journal of Pharmacology, vol. 101, pp. 247 (1990)), while it is also published to exhibit central actions, such as memory, anxiety, etc. (Brain Research, vol. 503, pp. 73 (1989); Peptides, vol. 19, pp. 359 (1998)).

In light of the fact that the NPY Y3 receptor exists mainly in the brainstem and heart, NPY is reported to be involved in the control of blood pressure and heart rate (The Journal of Pharmacology and Experimental Therapeutics, vol. 258, pp. 633 (1991); Peptides, vol. 11, pp. 545 (1990)). Furthermore, NPY is found to be implicated in the secretion of catecholamine in the adrenal glands (The Journal of Pharmacology and Experimental Therapeutics, vol. 244, pp. 468 (1988); Life Sciences, vol. 50, pp. PL7 (1992)).

Since the NPY Y4 receptor shows particularly enhanced affinity for the pancreatic polypeptide, NPY, with regard to its pharmacologic activities, is reported to suppress pancreatic exocrine secretion and gastro-intestinal motility (Gastroenterology, vol. 85, pp. 1411 (1983)), while it is known to promote the secretion of sex hormones in the central nervous systems (Endocrinology, vol. 140, pp. 5171 (1999)).

As for the actions mediated by the NPY Y5 receptor, NPY exhibits a profound fat accumulating action including an orexigenic action (Nature, vol. 382, pp. 168 (1996); American Journal of Physiology, vol. 277, pp. R1428 (1999)); there are reported its central actions, such as its involvement in the seizure and epilepsy, its implication in pain or the withdrawal symptoms owing to suspension of the morphine administration or use and its control of the circadian rhythm (Nature Medicine, vol. 3, pp. 761 (1997); Proceedings of the National Academy of Sciences of the United States of America, Vol. 96, pp. 13518 (1999); The Journal of Pharmacology and Experimental Therapeutics, vol. 284, pp. 633 (1998); The Journal of Neuroscience, vol. 21, pp. 5367 (2001)); and it is found to diuresis effect and hypoglicemic effect in the periphery (British Journal of Pharmacology, vol. 120, pp. 1335 (1998); Endocrinology, vol. 139, pp. 3018 (1998)), while it is furthermore reported to act to enhance cardiac hypertrophy caused by sthenia of the sympathetic nerve system (Proceedings of the National Academy of Sciences of the United States of America, vol. 97, pp. 1595 (2000)).

(1.3 mL), and the solution was admixed with water (0.13 mL), followed by stirring at room temperature for 48 hrs. The reaction mixture was neutralized with a 1N aqueous sodium hydroxide solution, followed by extraction with ethyl acetate. The organic layer was washed with an aqueous saturated sodium chloride solution, dried over anhydrous sodium sulfate and concentrated under reduced pressure. The residue was separated and purified on a collective thin-layer chromatograph (ethyl acetate:methanol=20:1) to give the title compound (15 mg).

$^{1}$HNMR (400 MHz, CDCl$_{3}$, δppm): 1.79-1.88 (2H, m) 1.97-2.05 (2H, m), 2.26-2.36 (2H, m), 3.10-3.22 (6H, m), 3.60-3.67 (1H, m), 4.11-4.17 (2H, m), 7.25-7.43 (5H, m), 7.52 (1H, s), 7.558 (2H, d, J=7.3 Hz); Mass spectrum (ESI): 397 (M+H)

Formulation Example 1

20.0 g of the Compound of Example 1, 417 g of lactose, 80 g of crystalline cellulose and 80 g of partial α-starch are blended using a V cone blender, and 3.0 g of magnesium stearate is added, followed by blending. The blended powder is compressed into 3,000 tablets in a conventional manner, each tablet having 7.0 mm in diameter and weighing 150 mg.

Contents Per Tablet (150 mg)

| The Compound of Example 1 | 5.0 mg |
|---|---|
| Lactose | 104.25 mg |
| Crystalline cellulose | 20.0 mg |
| Partial α-starch | 20.0 mg |
| Magnesium stearate | 0.75 mg |

Formulation Example 2

10.8 g of hydroxypropyl cellulose 2910 and 2.1 g of polyethylene glycol 6000 are dissolved in 172.5 g of purified water, and 2.1 g of titanium dioxide is dispersed in the solution to prepare a coating liquid. 2,500 tablets separately prepared in Formulation Example 1 are subjected to spray-coating with the coating liquid using HICOATER-MINI to give film-coated tablets each weighing 155 mg.

Contents Per Tablet (155 mg)

| The tablets of Formulation Example 1 | 150 mg |
|---|---|
| Hydroxypropylcellulose 2910 | 3.6 mg |
| Polyethylene glycol 6000 | 0.7 mg |
| Titanium dioxide | 0.7 mg |

INDUSTRIAL APPLICABILITY

Since compounds of the present invention exhibit NPY antagonistic effects especially on NPY Y5 receptors and show excellent pharmacokinetics such as transport into brain or transport to cerebrospinal fluid, etc., and they are highly safe, they are useful for the treatment of various diseases related to NPY, for example, cardiovascular disorders such as angina, acute or congestive heart failure, myocardial infarction, hypertension, nephropathy, electrolyte abnormality, vasospasm, atherosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipemia, gout, fatty liver, etc., genital or reproductive disorders such as infertility, preterm labor, sexual dysfunction, etc., gastro-intestinal disorders, respiratory disorder, inflammatory diseases or glaucoma, and the like, also for example, atherosclerosis, hypogonadism, hyperandrogenism, polycystic ovary syndrome, hirsutism, gastrointestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, (syndrome X), Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, gallbladder diseases, cancer (breast, endometrial, colon), breathlessness, hyperuricemia, impaired fertility, low back pain, or increased anesthetic risk, and the like; renal system diseases; renal abnormalities such as dysfunction in body fluid flow, abnormalities of material transportation, and renal failure; shock; arrhythmia; symptoms related to surge in sympathomimetic activity during or after operation on coronary artery or gastrointestinal tracts; diseases related to brain or central nervous system, such as cerebral infarction, neurodegeneration, cerebral stroke, cerebrovascular spasm or cerebral hemorrhage; symptoms related to pain or nociception; diseases related to abnormalities in gastrointestinal motility or secretion, such as various ileuses, urinary incontinence, and Crohn's disease; eating disorders such as anorexia and bulimia; inflammatory symptoms or diseases; asthma; bronchiole constriction; or diseases related to abnormal secretion of hormones such as luteinizing hormone, growth hormone, insulin, and luteotropic hormone.

What is claimed is:
1. A compound of the general formula (I):

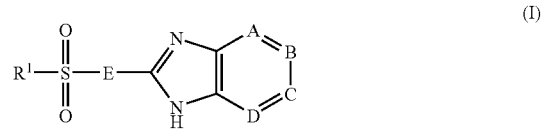

wherein:
A, B, C and D are each independently a methine group or a nitrogen atom, said methine group optionally having a substituent(s) selected from the group consisting of a halogen atom, a cyano group, a lower alkyl group, a C$_3$-C$_9$ cycloalkyl group, a halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N(R$^2$)R$^3$, and a group represented by —Q$^1$—Ar$^1$, wherein at least one of A, B, C and D is a methine group;
Ar$^1$ is an aryl group or a heteroaryl group, each of which may optionally have a substituent(s) selected from the group consisting of a halogen atom, a nitro group, a hydroxy group, a lower alkyl group, a halo-lower alkyl group, a hydroxy-lower alkyl group, a C$_3$-C$_6$ cycloalkyl group, a lower alkenyl group, a lower alkoxy group, a halo-lower alkoxy group, a lower alkylthio group, a lower alkylsulfonyl group, a carboxy group, a lower alkanoyl group, a lower alkoxycarbonyl group, a lower alkanoylamino group and a group represented by —Q²—Ar²;

Ar² is an aryl group or a heteroaryl group, each of which may optionally have a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group;

E is a group represented by the following formulae (E1):

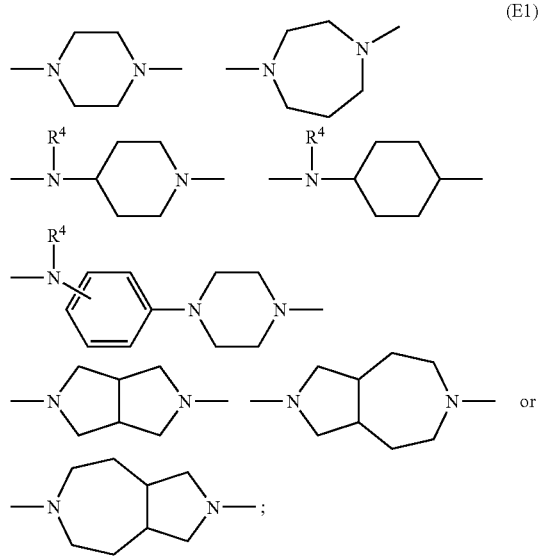

(E1)

R⁴ is a hydrogen atom, a lower alkyl group, an aralkyl group or an aryl group; Q¹ and Q² are each independently a single bond, an oxygen atom, a carbonyl group or a group represented by —N(R⁵)—;

R¹ is a lower alkyl group or an aryl group, said aryl group optionally having a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group, or is a lower alkylene group linked to linkable position(s) of E;

R² and R³ are each independently a hydrogen atom or a lower alkyl group, or are taken together to form a lower alkylene group which may be intervened by an oxygen atom, a sulfur atom or an imino group; and R⁵ is a hydrogen atom or a lower alkyl group;
or a pharmaceutically acceptable salt or ester thereof.

2. The compound of claim 1 wherein A and D are each independently an unsubstituted methine group or a nitrogen atom; one of B and C is a methine group having a halo-lower alkyl group or a group represented by —Q¹—Ar¹, and the other is an unsubstituted methine group or a nitrogen atom; or a pharmaceutically acceptable salt or ester thereof.

3. The compound of claim 1 wherein A, B and D are each independently an unsubstituted methine group; and C is a methine group having a halo-lower alkyl group or a group represented by —Q¹—Ar¹; or a pharmaceutically acceptable salt or ester thereof.

4. The compound of claim 1 wherein A is an unsubstituted methine group; one or both of B and D is a nitrogen atom; and C is a methine group having a halo-lower alkyl group or a group represented by —Q¹—Ar¹; or a pharmaceutically acceptable salt or ester thereof.

5. The compound of claim 1 wherein E is a group represented by the following formulae (E10):

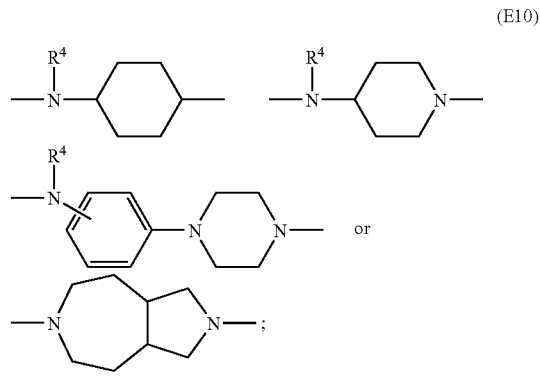

(E10)

and R⁴ is a hydrogen atom, a lower alkyl group, an aralkyl group or an aryl group;
or a pharmaceutically acceptable salt or ester thereof.

6. The compound of claim 1 wherein E is a group represented by the following formulae (E11):

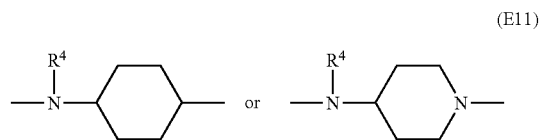

(E11)

and R⁴ is a hydrogen atom, a lower alkyl group, an aralkyl group or an aryl group;
or a pharmaceutically acceptable salt or ester thereof.

7. The compound of claim 1 wherein R¹ is a lower alkyl group;
or a pharmaceutically acceptable salt or ester thereof.

8. The compound of claim 1 which is selected from the group consisting of:

(1) 2-(trans-4-tert-butylsulfonylaminocyclohexyl)-5-(trifluoromethyl)benzimidazole;

(2) 2-(trans-4-tert-butylsulfonylaminocyclohexyl)-5-(2-methyltetrazol-5-yl)benzimidazole;

(3) 2-(trans-4-tert-butylsulfonylaminocyclohexyl)-5-phenylbenzimidazole;

(4) 2-(trans-4-tert-butylsulfonylaminocyclohexyl)-5-(2-fluorophenyl)imidazo[4,5-b]pyridine;

(5) 8-(trans-4-tert-butylsulfonylaminocyclohexyl)-2-(2-fluorophenyl)purine;

(6) 8-(cis-4-tert-butylsulfonylaminocyclohexyl)-2-(2-fluorophenyl)purine;

(7) 8-(trans-4-tert-butylsulfonylaminocyclohexyl)-2-(4-fluorophenyl)purine;

(8) 8-(cis-4-tert-butylsulfonylaminocyclohexyl)-2-(4-fluorophenyl)purine;

(9) 8-(trans-4-tert-butylsulfonylaminocyclohexyl)-2-phenylpurine;

(10) 8-(cis-4-tert-butylsulfonylaminocyclohexyl)-2-phenylpurine;

(11) 5-(2,4-difluorophenyl)-2-(trans-4-isopropylsulfonylaminocyclohexyl)-imidazo[4,5-b]pyridine;

(12) 5-(2,4-difluorophenyl)-2-(cis-4-isopropylsulfonylaminocyclohexyl)imidazo[4,5-b]pyridine;

(13) 2-(trans-4-methylsulfonylaminocyclohexyl)-5-phenylbenzimidazole;

(14) 5-phenyl-2-(trans-4-p-tolylsulfonylaminocyclohexyl)benzimidazole;

(15) 2-(cis-4-methylsulfonylaminocyclohexyl)-5-phenylbenzimidazole;

(16) 5-phenyl-2-(cis-4-p-tolylsulfonylaminocyclohexyl)benzimidazole;

(17) 2-{trans-4-(N-methyl-tert-butylsulfonylamino)cyclohexyl}-5-phenyl-benzimidazole;

(18) 2-(4-tert-butylsulfonylaminopiperidin-1-yl)-5-phenylbenzimidazole;

(19) 2-(4-tert-butylsulfonylaminopiperidin-1-yl)-5-(2-methyltetrazol-5-yl)benzimidazole;

(20) 2-(3-isopropylsulfonyl-cis-3,7-diazabicyclo[3.3.0]oct-7-yl)-5-phenylbenzimidazole:

(21) 2-(4-isopropylsulfonyl-cis-4,9-diazabicyclo[5.3.0]dec-9-yl)-5-phenylbenzimidazole;

(22) 2-(1-isopropylsulfonylpiperazin-4-yl)-5-phenylbenzimidazole;

(23) 8-{1-(2-methylsulfonylaminophenyl)piperazin-4-yl}-2-phenylpurine;

(24) 5-phenyl-2-{4-(N-phenylmethylsulfonylamino)piperidin-1-yl}-benzimidazole; and

(25) 2-{4-(1,1-dioxo-1λ⁶-isothiazolidin-2-yl)piperidin-1-yl}-5-phenylbenzimidazole;

or a pharmaceutically acceptable salt thereof.

9. A pharmaceutical composition comprising a therapeutically effective amount of a compound of the general formula (I):

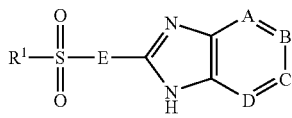

wherein:

A, B, C and D are each independently a methine group or a nitrogen atom, said methine group optionally having a substituent(s) selected from the group consisting of a halogen atom, a cyano group, a lower alkyl group, a $C_3$-$C_9$ cycloalkyl group, a halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N($R^2$)$R^3$, and a group represented by —$Q^1$—$Ar^1$, wherein at least one of A, B, C and D is a methine group;

$Ar^1$ is an aryl group or a heteroaryl group, each of which may optionally have a substituent(s) selected from the group consisting of a halogen atom, a nitro group, a hydroxy group, a lower alkyl group, a halo-lower alkyl group, a hydroxy-lower alkyl group, a $C_3$-$C_6$ cycloalkyl group, a lower alkenyl group, a lower alkoxy group, a halo-lower alkoxy group, a lower alkylthio group, a lower alkylsulfonyl group, a carboxy group, a lower alkanoyl group, a lower alkoxycarbonyl group, a lower alkanoylamino group and a group represented by —$Q^2$—$Ar^2$;

$Ar^2$ is an aryl group or a heteroaryl group, each of which may optionally have a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group;

E is a group represented by the following formulae (E1):

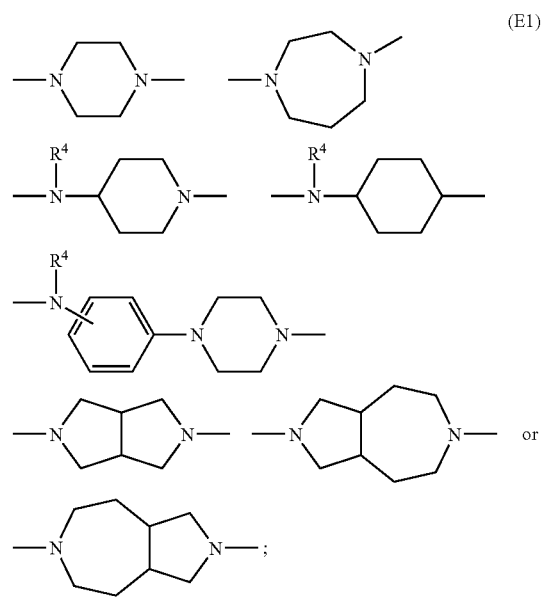

$R^4$ is a hydrogen atom, a lower alkyl group, an aralkyl group or an aryl group; $Q^1$ and $Q^2$ are each independently a single bond, an oxygen atom, a carbonyl group or a group represented by —N($R^5$)—;

$R^1$ is a lower alkyl group or an aryl group, said aryl group optionally having a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group, or is a lower alkylene group linked to linkable position(s) of E;

$R^2$ and $R^3$ are each independently a hydrogen atom or a lower alkyl group, or are taken together to form a lower alkylene group which may be intervened by an oxygen atom, a sulfur atom or an imino group; and $R^5$ is a hydrogen atom or a lower alkyl group, as an active ingredient;

or a pharmaceutically acceptable salt or ester thereof; and a pharmaceutically acceptable additive.

10. A method for the treatment of bulimia, obesity or diabetes, which comprises administering to a mammal in need thereof a compound of the general formula (I):

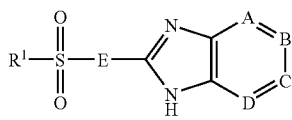
(I)

wherein:
- A, B, C and D are each independently a methine group or a nitrogen atom, said methine group optionally having a substituent(s) selected from the group consisting of a halogen atom, a cyano group, a lower alkyl group, a $C_3$-$C_9$ cycloalkyl group, a halo-lower alkyl group, a hydroxy group, a lower alkoxy group, a halo-lower alkoxy group, a lower alkoxycarbonyl group, a lower alkylsulfonyl group, a lower alkylsulfonyloxy group, a group represented by —N($R^2$)$R^3$, and a group represented by —$Q^1$—$Ar^1$, wherein at least one of A, B, C and D is a methine group;
- $Ar^1$ is an aryl group or a heteroaryl group, each of which may optionally have a substituent(s) selected from the group consisting of a halogen atom, a nitro group, a hydroxy group, a lower alkyl group, a halo-lower alkyl group, a hydroxy-lower alkyl group, a $C_3$-$C_6$ cycloalkyl group, a lower alkenyl group, a lower alkoxy group, a halo-lower alkoxy group, a lower alkylthio group, a lower alkylsulfonyl group, a carboxy group, a lower alkanoyl group, a lower alkoxycarbonyl group, a lower alkanoylamino group and a group represented by —$Q^2$—$Ar^2$;
- $Ar^2$ is an aryl group or a heteroaryl group, each of which may optionally have a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group;
- E is a group represented by the following formulae (E1):

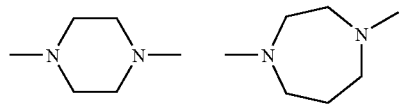
(E1)

-continued

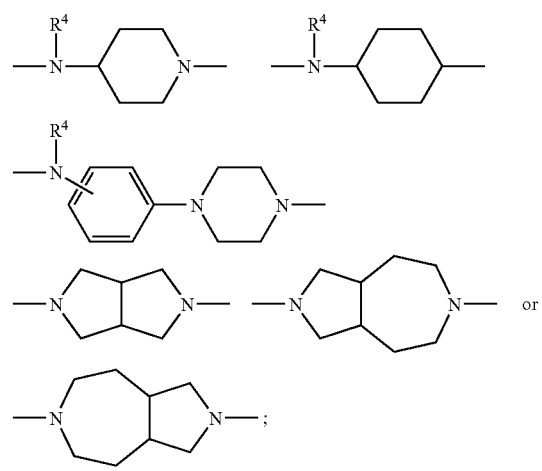

- $R^4$ is a hydrogen atom, a lower alkyl group, an aralkyl group or an aryl group; $Q^1$ and $Q^2$ are each independently a single bond, an oxygen atom, a carbonyl group or a group represented by —N($R^5$)—;
- $R^1$ is a lower alkyl group or an aryl group, said aryl group optionally having a substituent(s) selected from the group consisting of a halogen atom, a cyano group, a lower alkyl group, a halo-lower alkyl group, a hydroxy-lower alkyl group, a hydroxy group, a lower alkoxy group, a halo-lower alkoxy group, a lower alkylamino group, a di-lower alkylamino group, a lower alkanoyl group and an aryl group, or is a lower alkylene group linked to linkable position(s) of E;
- $R^2$ and $R^3$ are each independently a hydrogen atom or a lower alkyl group, or are taken together to form a lower alkylene group which may be intervened by an oxygen atom, a sulfur atom or an imino group; and
- $R^5$ is a hydrogen atom or a lower alkyl group;

or a pharmaceutically acceptable salt or ester thereof.

* * * * *